(12) United States Patent
Gagnon et al.

(10) Patent No.: US 11,413,002 B2
(45) Date of Patent: Aug. 16, 2022

(54) APPARATUS AND METHODS FOR SCALABLE FIELD OF VIEW IMAGING USING A MULTI-SOURCE SYSTEM

(71) Applicant: Accuray, Inc., Sunnyvale, CA (US)

(72) Inventors: Daniel Gagnon, Twinsburg, OH (US); Zhicong Yu, Highland Hts., OH (US); Jacob Shea, Madison, WI (US)

(73) Assignee: ACCURAY INC., Sunnyvale, CA (US)

( * ) Notice: Subject to any disclaimer, the term of this patent is extended or adjusted under 35 U.S.C. 154(b) by 182 days.

(21) Appl. No.: 16/694,148

(22) Filed: Nov. 25, 2019

(65) Prior Publication Data

US 2020/0170590 A1 Jun. 4, 2020

Related U.S. Application Data

(60) Provisional application No. 62/878,364, filed on Jul. 25, 2019, provisional application No. 62/843,796, (Continued)

(51) Int. Cl.
*G06T 11/00* (2006.01)
*A61B 6/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01); *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01);
(Continued)

(58) Field of Classification Search
CPC .................................................. A61N 5/1049
See application file for complete search history.

(56) References Cited

U.S. PATENT DOCUMENTS

| | | | |
|---|---|---|---|
| 4,190,773 A | 2/1980 | Braden et al. | |
| 5,615,279 A | 3/1997 | Yoshioka et al. | |

(Continued)

FOREIGN PATENT DOCUMENTS

| | | |
|---|---|---|
| DE | 10 2006 007058 A1 | 7/2007 |
| EP | 1062914 A1 | 12/2000 |

(Continued)

OTHER PUBLICATIONS

International Search Report and Written Opinion from PCT/US2019/063080 dated Mar. 16, 2020.

(Continued)

*Primary Examiner* — Dani Fox
(74) *Attorney, Agent, or Firm* — Calfee, Halter & Griswold LLP

(57) ABSTRACT

Multimodal imaging apparatus and methods include a rotatable gantry system with multiple sources of radiation comprising different energy levels (for example, kV and MV). Fast slip-ring technology and helical scans allow data from multiple sources of radiation to be combined or utilized to generate improved images and workflows, including for IGRT. Features include large field-of-view (LFOV) MV imaging, kV region-of-interest (ROI) imaging, and scalable field-of-view (SFOV) dual energy imaging.

21 Claims, 16 Drawing Sheets

Related U.S. Application Data filed on May 6, 2019, provisional application No. 62/836,352, filed on Apr. 19, 2019, provisional application No. 62/836,357, filed on Apr. 19, 2019, provisional application No. 62/821,116, filed on Mar. 20, 2019, provisional application No. 62/813,335, filed on Mar. 4, 2019, provisional application No. 62/801,260, filed on Feb. 5, 2019, provisional application No. 62/800,287, filed on Feb. 1, 2019, provisional application No. 62/796,831, filed on Jan. 25, 2019, provisional application No. 62/773,712, filed on Nov. 30, 2018, provisional application No. 62/773,700, filed on Nov. 30, 2018.

(51) Int. Cl.
| | |
|---|---|
| *A61B 6/03* | (2006.01) |
| *A61B 6/06* | (2006.01) |
| *A61B 6/02* | (2006.01) |
| *A61N 5/10* | (2006.01) |
| *A61B 6/08* | (2006.01) |
| *G06T 7/30* | (2017.01) |
| *A61B 5/055* | (2006.01) |
| *A61B 6/04* | (2006.01) |

(52) U.S. Cl.
CPC ............. *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | | |
|---|---|---|---|
| 6,233,478 | B1 | 5/2001 | Liu |
| 6,307,909 | B1 | 10/2001 | Flohr et al. |
| 7,050,528 | B2 | 5/2006 | Chen |
| 7,108,421 | B2 | 9/2006 | Gregerson et al. |
| 7,336,759 | B2 | 2/2008 | Nukui |
| 7,660,380 | B2 | 2/2010 | Boese et al. |
| 8,116,430 | B1 | 2/2012 | Shapiro et al. |
| 8,467,497 | B2 | 6/2013 | Lu et al. |
| 8,588,363 | B2 | 11/2013 | Flohr |
| 9,400,332 | B2 | 7/2016 | Star-Lack et al. |
| 2003/0007601 | A1 | 1/2003 | Jaffray et al. |
| 2003/0076927 | A1 | 4/2003 | Shigeyuki et al. |
| 2004/0091079 | A1 | 5/2004 | Zapalac |
| 2004/0102688 | A1 | 5/2004 | Walker et al. |
| 2004/0202360 | A1 | 10/2004 | Besson |
| 2005/0053188 | A1 | 3/2005 | Gohno |
| 2005/0251029 | A1 | 11/2005 | Khamene et al. |
| 2006/0109954 | A1 | 5/2006 | Gohno |
| 2006/0262894 | A1 | 11/2006 | Bernhadt et al. |
| 2007/0127621 | A1 | 6/2007 | Grass et al. |
| 2007/0189444 | A1 | 8/2007 | Van Steven-Daal et al. |
| 2008/0103834 | A1 | 5/2008 | Reiner |
| 2008/0112532 | A1 | 5/2008 | Schlomka et al. |
| 2009/0080603 | A1 | 3/2009 | Shukla et al. |
| 2009/0135994 | A1 | 5/2009 | Yu et al. |
| 2009/0161826 | A1 | 6/2009 | Gertner et al. |
| 2009/0225932 | A1 | 9/2009 | Zhu et al. |
| 2009/0283682 | A1 | 11/2009 | Star-Lack et al. |
| 2009/0304142 | A1 | 12/2009 | Ruimi et al. |
| 2010/0046819 | A1 | 2/2010 | Noo et al. |
| 2010/0142791 | A1 | 6/2010 | Tsuji |
| 2010/0208964 | A1 | 8/2010 | Wiegert et al. |
| 2011/0142312 | A1 | 6/2011 | Toth et al. |
| 2011/0255656 | A1 | 10/2011 | Star-Lack et al. |
| 2012/0014582 | A1 | 1/2012 | Schaefer et al. |
| 2012/0207370 | A1 | 8/2012 | Fahimian et al. |
| 2012/0263360 | A1 | 10/2012 | Zhu et al. |
| 2012/0294504 | A1 | 11/2012 | Kyriakou |
| 2013/0101082 | A1 | 4/2013 | Jordan et al. |
| 2013/0294570 | A1 | 11/2013 | Hansis |
| 2014/0018671 | A1 | 1/2014 | Li et al. |
| 2014/0086383 | A1 | 3/2014 | Huwer et al. |
| 2014/0169652 | A1 | 6/2014 | Vic et al. |
| 2015/0297165 | A1 | 10/2015 | Tanaka et al. |
| 2015/0305696 | A1 | 10/2015 | Yamakawa et al. |
| 2016/0016009 | A1 | 1/2016 | Manzke et al. |
| 2016/0120486 | A1 | 5/2016 | Goto et al. |
| 2016/0220844 | A1 | 8/2016 | Paysan et al. |
| 2016/0262709 | A1 | 9/2016 | Siewerdsen et al. |
| 2017/0000428 | A1 | 1/2017 | Goto |
| 2017/0197098 | A1 | 7/2017 | Hirasawa et al. |
| 2017/0205360 | A1 | 7/2017 | Cinquin et al. |
| 2017/0278277 | A1 | 9/2017 | Morf et al. |
| 2017/0332982 | A1 | 11/2017 | Koehler et al. |
| 2018/0028143 | A1 | 2/2018 | Wiggers et al. |
| 2018/0070894 | A1 | 3/2018 | Osaki et al. |
| 2018/0192978 | A1 | 7/2018 | Naylor |
| 2018/0345042 | A1 | 12/2018 | Voronenko et al. |
| 2019/0099149 | A1 | 4/2019 | Li |
| 2020/0016432 | A1* | 1/2020 | Maolinbay ............. A61B 6/032 |
| 2020/0121267 | A1 | 4/2020 | Deutschmann |
| 2020/0402644 | A1 | 12/2020 | Zhou et al. |
| 2021/0165122 | A1 | 6/2021 | Morton |

FOREIGN PATENT DOCUMENTS

| | | | |
|---|---|---|---|
| EP | 2383702 | A1 | 11/2011 |
| JP | H09 218939 | A | 8/1997 |
| JP | 2004 136021 | | 5/2004 |
| JP | 2008 036275 | | 2/2008 |
| WO | 2005112753 | A2 | 12/2005 |
| WO | 2006/078386 | A2 | 7/2006 |
| WO | 2010/014288 | A1 | 2/2010 |
| WO | 2010/099621 | A1 | 9/2010 |
| WO | 2015103184 | A1 | 7/2015 |
| WO | 2018/156968 | A1 | 8/2018 |
| WO | 2018/183748 | A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.

(56) References Cited

OTHER PUBLICATIONS

International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11, Radiology, vol. 279, No. 1 Apr. 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,145 dated Mar. 17, 2021, 10 pages.
Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,192 dated Jun. 10, 2021, 10 pages.
Office Action from U.S. Appl. No. 16/694,202 dated Apr. 9, 2021, 12 pages.
Restriction Requirement from U.S. Appl. No. 16/694,210 dated Jun. 10, 2021, 6 pages.
Office Action from U.S. Appl. No. 16/694,218 dated Apr. 15, 2021, 7 pages.
Office Action from U.S. Appl. No. 16/694,230 dated Apr. 1, 2021, 6 pages.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging Physics in Medicine and Biology, pp. 6729-6748, vol. 51.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al.. Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Office Action from U.S. Appl. No. 16/694,161 dated Sep. 13, 2021, 18 pages.
Zhu, et al. Noise suppression in scatter correction for cone-beam CT, American Association of Physicists in Medicine, 2009, pp. 741-752, vol. 36, No. 3.
Anas, et al. High-quality 3D correction of ring and radiant artifacts in flat panel detector-based cone beam volume CT imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, pp. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.

\* cited by examiner

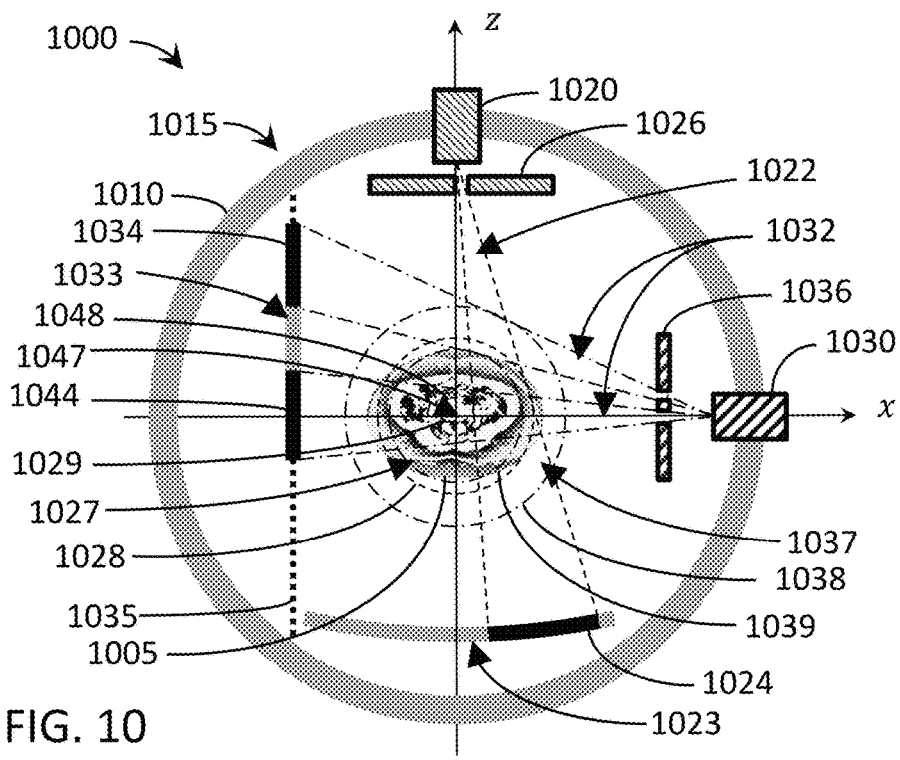
FIG. 10
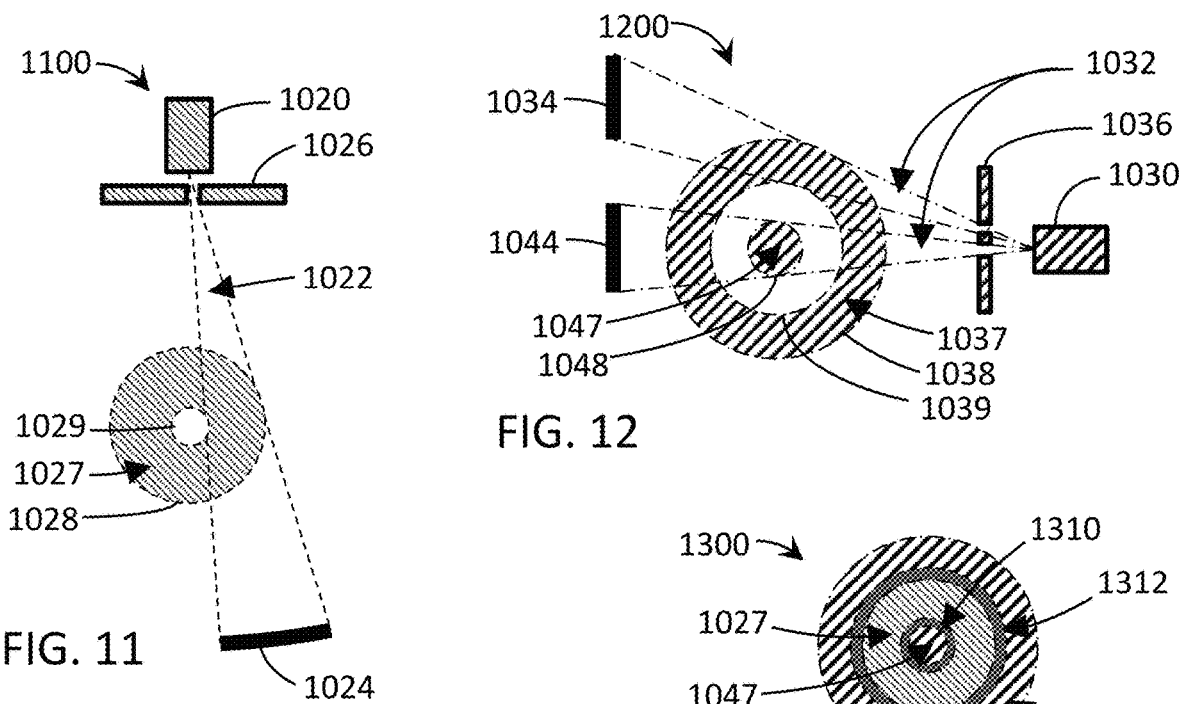
FIG. 11
FIG. 12
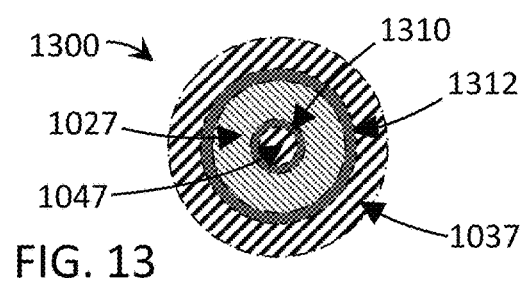
FIG. 13

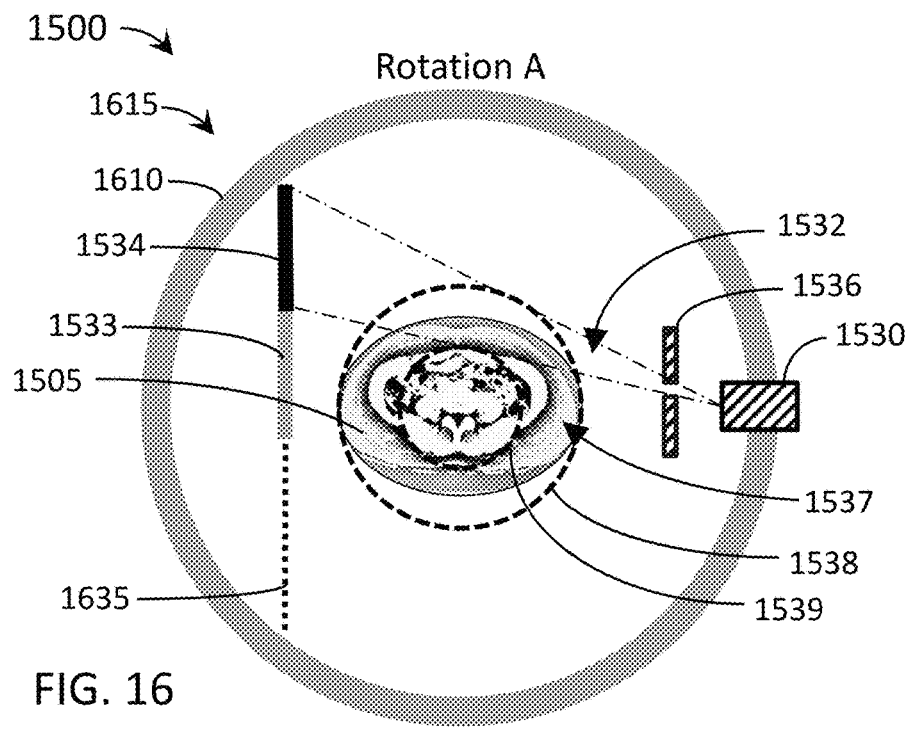
FIG. 16
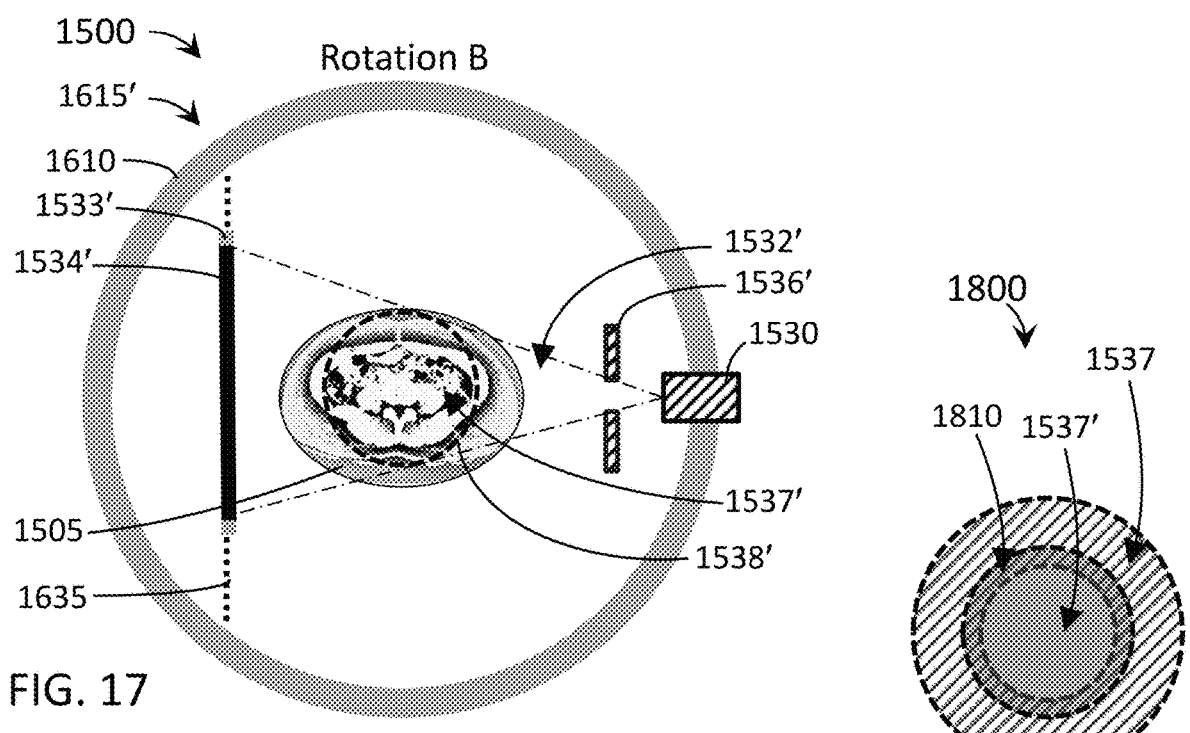
FIG. 17
FIG. 18

APPARATUS AND METHODS FOR SCALABLE FIELD OF VIEW IMAGING USING A MULTI-SOURCE SYSTEM

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled ";" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to utilizing multimodal radiation for imaging, and, more particularly, utilizing low-energy radiation (e.g., kilovolt x-ray (kV)) and high-energy radiation (e.g., megavolt x-ray (MV)) in combination for improved imaging, including for scalable fields-of-view during computed tomography (CT) scans.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a therapeutic radiation source, such as a linear accelerator (LINAC), to generate radiation beams, such as x-rays. In one type of external beam radiation therapy, a therapeutic radiation source directs a sequence of x-ray beams at a tumor site from multiple angles in the field of view. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centigray) and hypo-fractionation (e.g., one to five fractions or treatment days). Radiotherapy is typically characterized by a low dose per fraction (e.g., 100-200 centigray) and hyper-fractionation (e.g., 30 to 45 fractions). For convenience, the terms "radiation treatment" and "radiation therapy" are used interchangeably herein to mean radiosurgery and/or radiotherapy unless otherwise noted.

Image-guided radiation therapy (IGRT) systems include gantry-based systems and robotic arm-based systems. In gantry-based systems, a gantry rotates the therapeutic radiation source around an axis passing through the isocenter. Gantry-based systems include C-arm gantries, in which the therapeutic radiation source is mounted, in a cantilever-like manner, and rotates about the axis passing through the isocenter. Gantry-based systems further include ring gantries having generally toroidal shapes in which the patient's body extends through a bore of the ring/toroid, and the therapeutic radiation source is mounted on the perimeter of the ring and rotates about the axis passing through the isocenter. Traditional gantry systems (ring or C-arm) deliver therapeutic radiation with a set angle defined by the rotational trajectory of the radiation source. In robotic arm-based systems, the therapeutic radiation source is mounted on an articulated robotic arm that extends over and around the patient, the robotic arm being configured to provide at least five degrees of freedom. Robotic arm-based systems provide the capability to deliver therapeutic radiation from multiple out-of-plane directions, i.e., are capable of non-coplanar delivery.

Associated with each radiation therapy system is an imaging system to provide in-treatment images that are used to set up and, in some examples, guide the radiation delivery procedure and track in-treatment target motion. MV imaging systems can place a detector opposite the therapeutic source to image the patient for setup and in-treatment images, while other approaches utilize distinct, independent image radiation source(s) and/or detector(s) for the patient set-up and in-treatment images. Target or target volume tracking during treatment is accomplished by comparing in-treatment images to prior or pre-treatment image information. Pre-treatment image information may comprise, for example, CT data, cone-beam CT (CBCT) data, magnetic resonance imaging (MRI) data, positron emission tomography (PET) data or 3D rotational angiography (3DRA) data, and any information obtained from these imaging modalities (for example and without limitation, digitally reconstructed radiographs (DRRs)).

In one common scenario, the therapeutic source is a LINAC producing therapeutic radiation (which can be, e.g., a MV source) and the imaging system comprises one or more independent x-ray imaging sources producing lower energy imaging radiation (each of which can be, e.g., a kV source). In-treatment images can comprise one or more (preferably at least two) two-dimensional images (typically x-ray) acquired at one or more different points of view (e.g., stereoscopic x-ray images), and can be compared, for example, to two-dimensional DRRs derived from the three dimensional pre-treatment image information. A DRR is a synthetic x-ray image generated by casting hypothetical x-rays through the 3D imaging data, where the direction and orientation of the hypothetical x-rays simulate the geometry of the in-treatment x-ray imaging system. The resulting DRR then has approximately the same scale and point of view as the in-treatment x-ray imaging system, and can be compared with the in-treatment x-ray images to determine the position and orientation of the target, which can then be used to guide delivery of radiation to the target.

In another common scenario, either the therapeutic radiation source or an independent x-ray imaging source (e.g., a kV source) mounted on the gantry is used to acquire multiple views and reconstruct a volumetric image—a CT image. Views—also called projections—are acquired for at least 180 degrees plus the imaging beam fan angle to provide full mathematical support for reconstructing a 3-D volume or individual axial slices. The imaging detector mounted opposite the x-ray source can be a single row detector used to acquire data for a single slice at a time, or a multi-row detector or fully 2-D flat panel detector to acquire data for many slices at once.

CBCT has also been proposed as an in-treatment imaging modality for use in conjunction with radiation treatment systems, in some cases as a kV imaging modality and in other cases as a MV (portal) imaging modality. Prior to treatment, a CBCT planning image could be acquired for treatment planning. Subsequently, before each treatment fraction, a CBCT image could be acquired and compared to the CBCT pre-treatment planning image, and the results of the comparison used to modify the treatment plan for that treatment fraction to compensate for interfraction setup errors and/or interfraction organ motion.

Whereas conventional CT imaging reconstructs 2D slices from 1D projections through a target volume, the 2D slices then being stacked to form a 3D volumetric image, CBCT imaging directly constructs a 3D volumetric image from 2D projections of the target volume. As known in the art, CBCT offers the ability to form a 3D image volume from a single gantry rotation (more specifically, a rotation of at least 180 degrees plus a fan beam angle) about the target volume, whereas conventional CT requires one rotation per slice (for single-row detectors) or 1/M rotations per slice (for quasi-linear multi-row detectors having M rows). CBCT also provides for a more isotropic spatial resolution, whereas conventional CT limits the spatial resolution in the longitudinal direction to the slice thickness. However, because conventional CT systems usually offer a substantially higher degree of collimation near their linear or quasi-linear row detectors than can usually be afforded by CBCT systems near their two-dimensional detectors, scattering noise and artifacts are more of a problem for CBCT systems than for conventional CT systems. Another major issue with (single rotation, non-helical) CBCT (other than scatter) is insufficient sampling on all slices except for the central slice (the plane containing the source trajectory).

There are also cases where projection data are laterally truncated (i.e. the projection data capture only a fraction of the transaxial extent of the object). For example, the transaxial field-of-view (FOV) of a typical CT system ranges from 40 cm to 70 cm, which sometimes is not large enough to cover the entire patient and causes data truncation in the lateral direction. Another example is small region-of-interest (ROI) imaging for reduced x-ray scatter contamination (and thus enhanced soft-tissue visibility). Such lateral truncation in projection data poses an insufficient-data problem and results in significantly biased CT number in the reconstructed image.

Solutions to adequately address laterally truncated data for extended FOV CT are needed. Because most CT scanners have a single x-ray source, approximating the missing data by extrapolating the available data is possible but inadequate. Such approximations may involve assumptions of the shape and material of the scan object or the shape of the projection data. More advanced approximations may involve data consistency conditions or issues.

BRIEF SUMMARY

In one embodiment, a multimodal imaging apparatus includes a rotatable gantry system positioned at least partially around a patient support, a first radiation source coupled to the rotatable gantry system, the first radiation source configured for imaging radiation, a first beamformer configured to adjust a shape of a first radiation beam emitted by the first radiation source, a second radiation source coupled to the rotatable gantry system, the second radiation source configured for at least one of imaging radiation or therapeutic radiation, wherein the second radiation source comprises an energy level more than the first radiation source, a second beamformer configured to adjust a shape of a second radiation beam emitted by the second radiation source, and at least one radiation detector coupled to the rotatable gantry system and positioned to receive radiation from at least one of the first radiation source or the second radiation source, where the apparatus acquires first measured projection data associated with a first region of a patient from the first radiation source and second measured projection data associated with a second region of the patient from the second radiation source during a scan.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

FIG. 10 shows an illustration of an exemplary multimodal scan configuration projecting through an exemplary patient in a transaxial plane.

FIG. 11 shows an illustration of the MV subsystem of the exemplary multimodal scan configuration shown in FIG. 10.

FIG. 12 shows an illustration of the kV subsystem of the exemplary multimodal scan configuration shown in FIG. 10.

FIG. 13 shows an illustration of the various FOV regions created by the multimodal scan configuration shown in FIG. 10 in a superimposed view.

FIG. 16 shows an illustration of the exemplary kV radiation source during the multimodal scan configuration shown in FIG. 15 projecting through the exemplary patient in a transaxial plane during an exemplary rotation.

FIG. 17 shows an illustration of the exemplary kV radiation source during the multimodal scan configuration shown in FIG. 15 projecting through the exemplary patient in the transaxial plane during another exemplary rotation.

FIG. 18 shows an illustration of the various FOV regions created by the kV radiation source shown in FIGS. 16 and 17 in a superimposed view.

DETAILED DESCRIPTION

Figure 1:
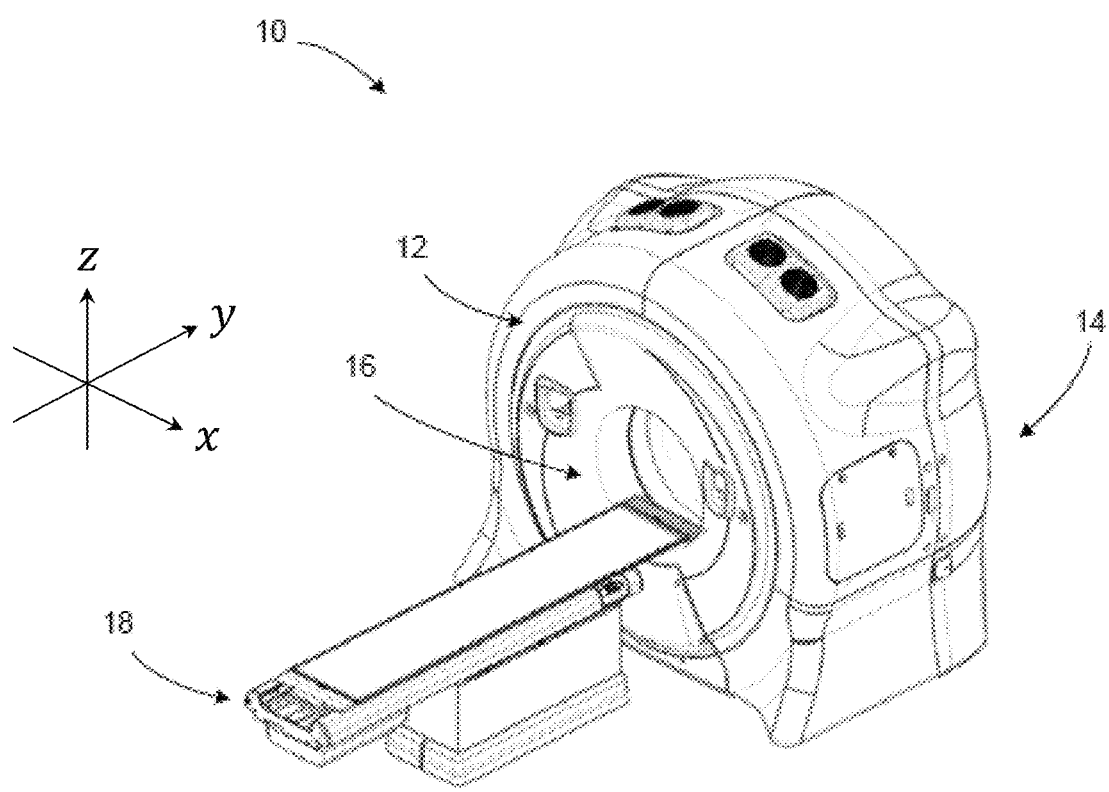
FIG. 1 is a perspective view of an exemplary multimodal radiotherapy apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multimodal imaging/radiotherapy devices and methods. In some embodiments, a radiotherapy delivery device and method can make use of an integrated low-energy radiation source for imaging and a high-energy radiation source for treatment and/or imaging in conjunction with or as part of IGRT. In particular, for example, a radiotherapy delivery device and method can combine a low-energy collimated radiation source for imaging in a gantry using rotational (e.g., helical or step-and-shoot) image acquisition along with a high-energy radiation source for imaging and/or therapeutic treatment. Complementary information and advantages can be exploited from a low-energy radiation source (e.g., kV) and from a high-energy radiation source (e.g., MV). For example, the intrinsic contrast of soft tissues may be higher at low-energies, while there is no starvation of primary photons through wide or dense structures at high-energies. KV and MV imaging data can be used to supplement each other to yield higher quality images. High quality volume imaging can be needed for visualization of targets and organs-at-risk (OARS), for adaptive therapy monitoring, and for treatment planning/replanning. In some embodiments, the multimodal system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the multimodal apparatus collimates a radiation source, including, for example, into a cone beam or a fan beam using, for example, a beamformer (which may include a collimator) to limit the beam. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high frame rates, and/or sparse data reconstruction techniques, to provide CT quality imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

The multimodal apparatus and methods can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). Also, exposing only a primary region of the detector to direct radiation allows shadowed regions of the detector to receive only scatter. In some embodiments, scatter measurements in the shadow region (and in some embodiments measurements in the penumbra region) of the detector can be used to estimate scatter in the primary region of the detector receiving projection data.

The multimodal apparatus and method can provide selective and variable detector readout areas and ranges, including adjusting the detector readout range to limit the active area of the detector for improved readout speed. For example, less than the available shadow region data may be read and used for scatter estimation. Combining selective readout with beamforming allows for various optimizations of scatter fitting techniques.

Figure 2:
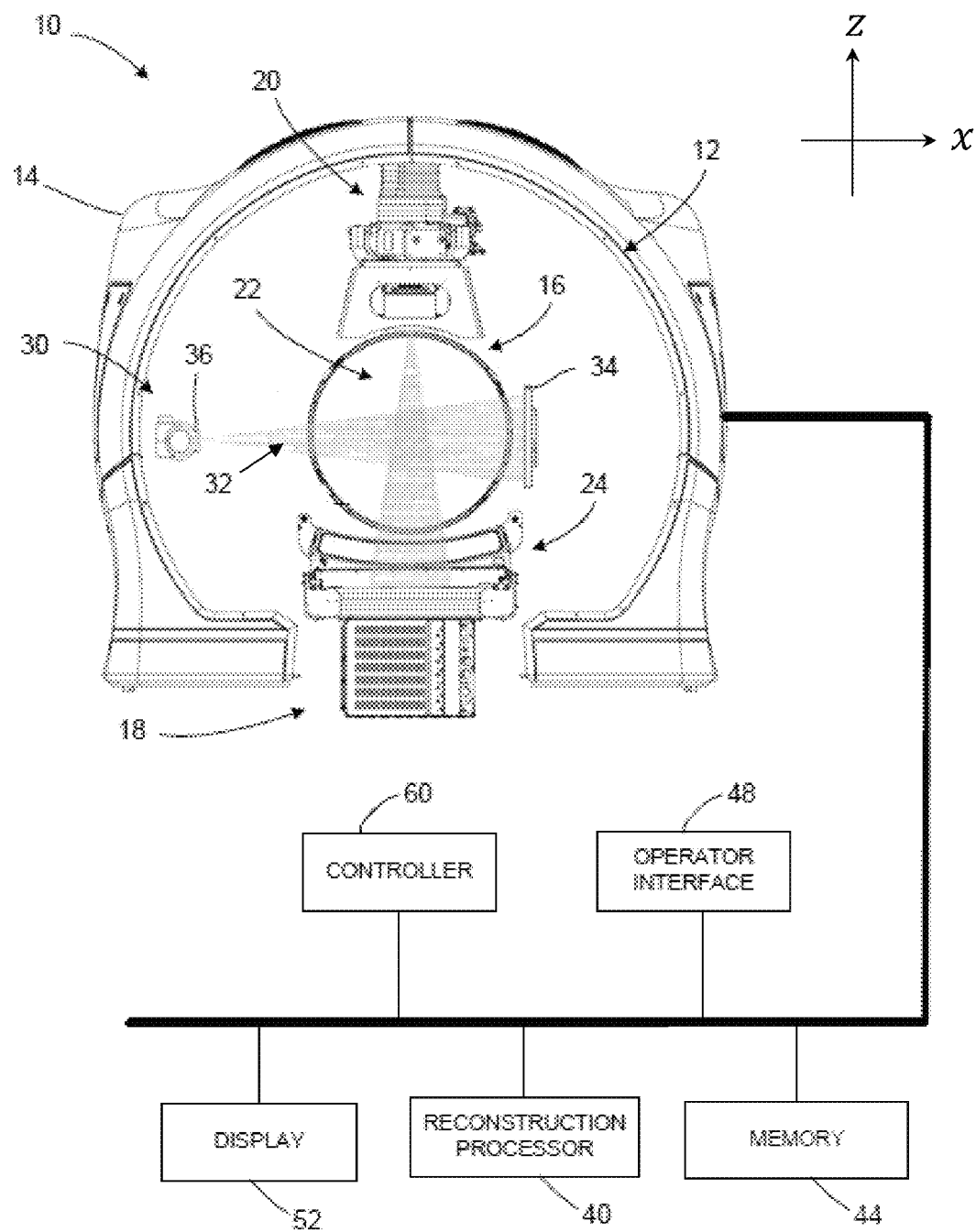
FIG. 2 is a diagrammatic illustration of an exemplary multimodal radiotherapy apparatus in accordance with one aspect of the disclosed technology.

With reference to FIG. 1 and FIG. 2, a multimodal apparatus 10 is shown. It will be appreciated that the multimodal apparatus 10 may be associated with and/or integrated into a radiotherapy device (as shown in FIG. 2) that can be used for a variety of applications, including, but not limited to IGRT, for example, as an IGRT delivery system (e.g., IGRT delivery system 104 shown in FIG. 3 and discussed in detail below). The multimodal apparatus 10 includes a rotatable gantry system, referred to as gantry 12, supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of radiation sources and associated radiation detector(s) while providing sufficient bandwidth for the high-quality imaging data received by the detector(s). A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system. As mentioned above, a major issue with single rotation CBCT is insufficient sampling on all slices except for the central slice (the one containing the rotation). This can be overcome by helical trajectory cone-beam imaging.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

As shown in FIG. 2, the multimodal apparatus 10 includes a low-energy radiation source (e.g., kV) 30 coupled to or otherwise supported by the rotatable gantry 12. In this embodiment, the low-energy radiation source 30 is a source of imaging radiation and emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30.

It will be appreciated that the x-ray detector 34 can take on a number of configurations without departing from the scope of the disclosed technology. As illustrated in FIG. 2, the x-ray detector 34 can be configured as a flat-panel detector (e.g., a multi-row flat panel detector). In accordance with another exemplary embodiment, the x-ray detector 34 can be configured as a curved detector. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the low-energy radiation source 30 rotates around and emits radiation toward the patient.

Although FIGS. 1 and 2 depict a multimodal apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and/or translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which may be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out, including, for example, combinations of narrow and wide FOV scans. The apparatus 10 has the ability to acquire both single rotation cone beam and wide and narrow beam angle cone beam images, helical or other.

The beamformer 36 may be configured in a variety of ways that allow it to adjust the shape of the radiation beam 32 emitted by the x-ray source 30. For example, the beamformer 36 can be configured to include a set of jaws or other suitable members that define and selectively adjust the size of an aperture through which the radiation beam from the x-ray source 30 may pass in a collimated manner. In accordance with one exemplary configuration, the beamformer 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2, the multimodal apparatus 10 may be integrated with a radiotherapy device that includes a high-energy radiation source (e.g., MV) 20 coupled to or otherwise supported by the rotatable gantry 12. In accordance with one embodiment, the high-energy radiation source 20 is configured as a source of therapeutic radiation, such as a high-energy source of radiation used for treatment of a tumor within a patient in a region of interest. In other embodiments, the high-energy radiation source 20 is also configured as a source of imaging radiation, or at least utilized as such. It will be appreciated that the source of therapeutic radiation can be a high-energy x-ray beam (e.g., MV x-ray beam), and/or a high-energy particle beam (e.g., a beam of electrons, a beam of protons, or a beam of heavier ions, such as carbon) or another suitable form of high-energy radiation. In one embodiment, the high-energy radiation source 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the high-energy radiation source 20 has a higher energy level (peak and/or average, etc.) than the low-energy radiation source 30.

In one embodiment, the high-energy radiation source 20 is a LINAC producing therapeutic radiation (e.g., MV) and the imaging system comprises an independent low-energy radiation source 30 producing relatively low intensity and lower energy imaging radiation (e.g., kV). In other embodiments, the therapeutic radiation source 20 could be a radioisotope, such as, for example, Co-60, which can generally have energy>1 MeV. The high-energy radiation source 20 can emit one or more beams of radiation (indicated generally by 22) toward a region-of-interest (ROI) within a patient supported on the patient support 18 in accordance with a treatment plan.

In various embodiments, the high-energy radiation source 20 is utilized as a source of therapeutic radiation and a source of imaging radiation. As discussed in detail below, sources of radiation 20, 30 may be used in conjunction with one another to provide higher quality and better utilized images. References to the therapeutic radiation source 20 herein are to distinguish the high-energy radiation source 20 from the low-energy radiation source 30, which may be used only for imaging. However, references to the therapeutic radiation source 20 include embodiments where the therapeutic radiation source 20 (high-energy radiation source) can be utilized for therapy and/or imaging. In other embodiments, at least one additional radiation source can be coupled to the rotatable gantry 12 and operated to acquire projection data at a peak photon energy distinct from the peak photon energies of sources of radiation 20, 30.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The beamformer associated with the therapeutic radiation source 20 can be configured in a number of ways, similar to the beamformer 36 associated with the imaging source 30. For example, a beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be incrementally reduced by offsetting the radiation planes. In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MV scatter on a kV detector.

When integrated with a radiotherapy device, multimodal apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, cone-beam CT data, MRI data, PET data or 3D rotational angiography (3DRA) data, and/or any information obtained from these or other imaging modalities. In some embodiments, the multimodal apparatus 10 can track in-treatment patient, target, or ROI motion.

A reconstruction processor 40 can be operatively coupled to detector 24 and/or detector 34. In one embodiment, the reconstruction processor 40 is configured to generate patient images based on radiation received by the detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The multimodal apparatus 10 can include an operator/user interface 48, where an operator of the apparatus 10 can interact with or otherwise control the apparatus 10 to provide input relating to scan or imaging parameters and the like. The operator interface 48 can include any suitable input devices, such as a keyboard, mouse, voice-activated controller, or the like. The apparatus 10 can also include a display 52 or other human-readable element to provide output to the operator of the apparatus 10. For example, the display 52 can allow the operator to observe reconstructed patient images and other information, such as imaging or scan parameters, related to operation of the apparatus 10.

As shown in FIG. 2, the multimodal apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, a multimodal apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with the apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with apparatus 10.

Multimodal apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented. For example, in various embodiments, the radiation sources 20, 30 can be operated such that the measured projection data from the radiation sources 20, 30 are acquired simultaneously (or essentially/nearly (quasi-) simultaneous, e.g., within about 50 ms of each other) or sequentially (e.g., separated by seconds, minutes, etc.)

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The multimodal apparatus 10 is capable of volume-based and planar-based imaging acquisitions. For example, in various embodiments, the multimodal apparatus 10 may be used to acquire volume images and/or planar images and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of apparatus 10 described above.

In one embodiment, the gantry 12 rotation speed, the patient support 18 speed, the beamformer shape, and/or the detector readout could all be constant during image acquisition. In other embodiments, one or more of these variables could change dynamically during image acquisition and/or treatment. The gantry 12 rotation speed, patient support 18 speed, beamformer shape, and/or detector readout can be varied to balance different factors, including, for example, image quality, image acquisition time, dosage, workflow, etc.

In other embodiments, these features can be combined with one or more other image-based activities or procedures, including, for example, patient set up, adaptive therapy monitoring, treatment planning, etc.

Figure 3:
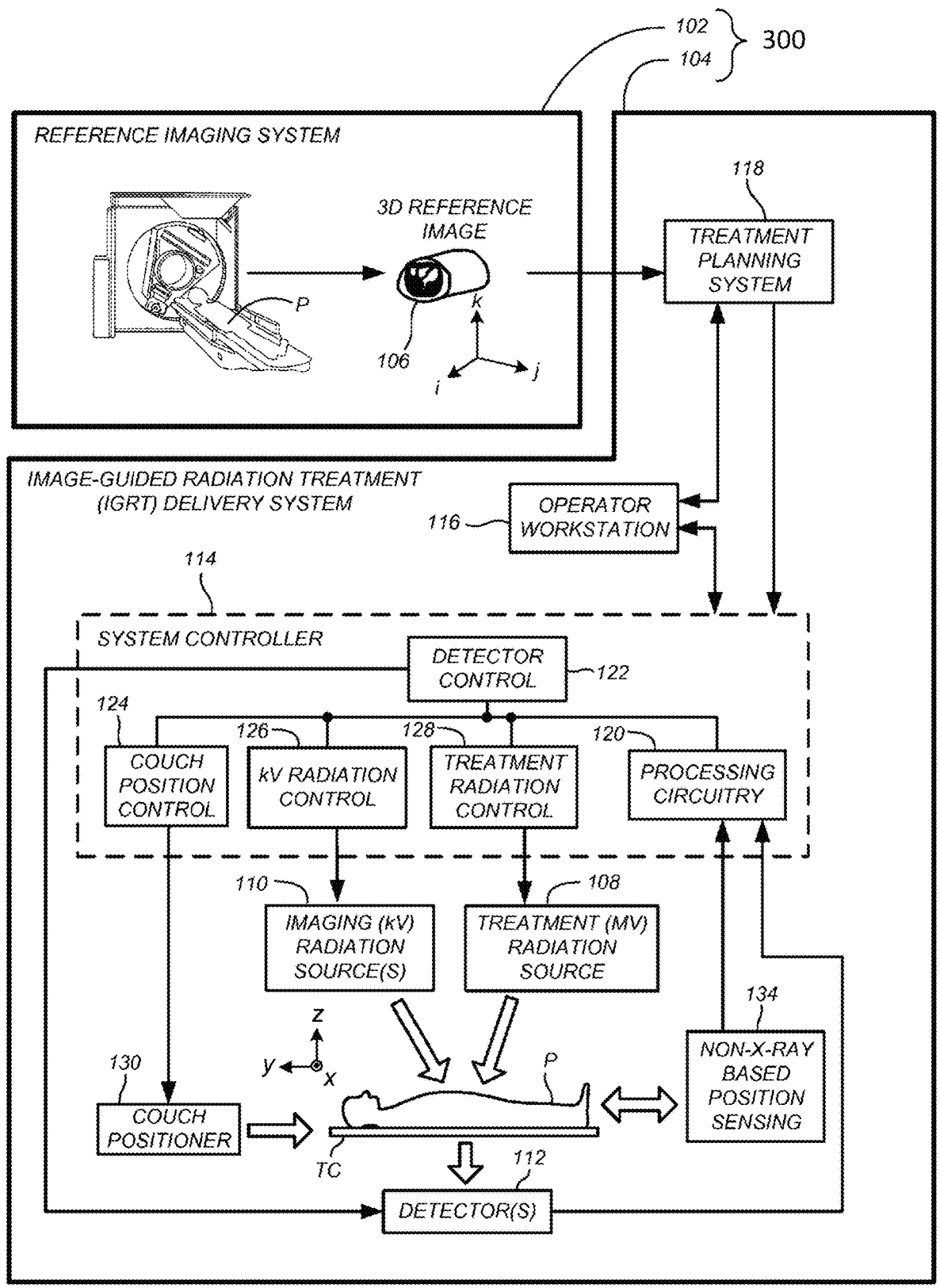
FIG. 3 illustrates an exemplary radiation treatment environment.

FIG. 3 illustrates an exemplary radiation treatment environment 300. The radiation treatment environment 300 includes a reference imaging system 102 and an IGRT system 104. The IGRT system 104 may comprise, for example, the multimodal apparatus 10 and its various components and devices as described above.

In one embodiment, the reference imaging system 102 can include a high precision volumetric imaging system such as, for example, a CT system or a MRI system. In view of cost and workflow considerations in many clinical environments, the reference imaging system 102 is often a general purpose tool used for a variety of different purposes in the clinic or hospital environment, and is not specifically dedicated to the IGRT system 104 or environment 300. Rather, the reference imaging system 102 may be located in its own separate room or vault and is purchased, installed, and/or maintained on a separate and more generalized basis than the IGRT system 104. Accordingly, for the embodiment of FIG. 3, the reference imaging system 102 is illustrated as being distinct from the IGRT system 104. In other embodiments, the reference imaging system 102 may be considered as an integral component of the IGRT system 104. For example, the multimodal apparatus 10 has the capability to act as the reference imaging system 102 and the IGRT system 104.

In this embodiment, IGRT system 104 comprises a high-energy radiation treatment (MV) source 108 that selectively applies high-energy x-ray treatment radiation to a target volume of a patient P positioned on a patient support or treatment couch TC. The MV source 108 applies the treatment radiation under the control of system controller 114, and in one embodiment, more particularly a treatment radiation control subsystem 128. System controller 114 further comprises processing circuitry 120, a detector controller 122, a couch position controller 124, and a kV radiation controller 126, each programmed and configured to achieve one or more of the functionalities described further herein. One or more imaging (kV) radiation sources 110 selectively emit relatively low-energy x-ray imaging radiation under the control of kV radiation controller 126, the imaging radiation being captured by one or more detectors 112. One or more of the detectors 112 can capture high-energy x-ray treatment radiation from MV source 108 that has propagated through the target volume.

Each kV radiation source 110 and the MV radiation source 108 have a precisely measurable and/or precisely determinable geometry relative to the (x, y, z) coordinate system of the IGRT system 104 and/or treatment room since they are dynamically moveable.

A couch positioner 130 can be actuated by the couch position controller 124 to position the couch TC. In some embodiments, a non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. IGRT system 104 further includes an operator workstation 116 and a treatment planning system 118.

In common clinical practice, treatment planning is performed on a pre-acquired treatment planning image or prior image data 106 generated by the reference imaging system 102. The pre-acquired treatment planning image 106 is often a high resolution three-dimensional CT image acquired substantially in advance (e.g., one to two days in advance) of the one or more radiation treatment fractions that the patient will undergo. As indicated in FIG. 3 by the illustration of an (i, j, k) coordinate system for the pre-acquired treatment planning image 106, which is in contrast to the (x, y, z) treatment room coordinate system illustrated for the treatment room of the IGRT system 104, there is generally no pre-existing or intrinsic alignment or registration between the treatment planning image 106 coordinate system and the treatment room coordinate system. During the treatment planning process, a physician typically establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the MV source 108 during each treatment fraction. Accurate delivery of therapeutic radiation to a target requires aligning the planning image coordinate system with the treatment room coordinate system, as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

In one embodiment, immediately prior to each treatment fraction, under image guidance via the kV imaging radiation source(s) 110, including according to one or more of the embodiments described further herein below, image-based pre-delivery steps may be performed. For example, the patient can be physically positioned or aligned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up or patient alignment. Depending on the location of the target volume, the target volume can vary in position and orientation and/or can undergo volumetric deformations due to patient movement and/or physiological cycles such as respiration. As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction.

A non x-ray based position sensing system 134 may also be provided. This non x-ray based position sensing system 134 may include, for example, external markers affixed in some manner to a patient's chest which move in response to respiration, which can precisely determine target location. Other mechanisms for monitoring respiration may also be used. Other non-respiratory position sensing systems 134 may also be used, including, for example, quasi static positioning, EKG for cardiac gating, etc. System 134 can correlate motion of the external markers with target motion, as determined from, for example, mono or stereoscopic x-ray projections. Non x-ray based position sensing system 134, therefore, can permit system controller 114 to monitor external marker motion, use the correlation model to precisely predict where the target will be located in real time (e.g., ~60 Hz), and direct the treatment beam to the target. As treatment of the moving target progresses, additional x-ray images may be obtained and used to verify and update the correlation model.

As used herein, "registration" of medical images refers to the determination of a mathematical relationship between corresponding anatomical or other (e.g. fiducial) features appearing in those medical images. Registration can include, but is not limited to, the determination of one or more spatial transformations that, when applied to one or both of the medical images, would cause an overlay of the corresponding anatomical features. The spatial transformations can include rigid-body transformations and/or deformable transformations and can, if the medical images are from different coordinate systems or reference frames, account for differences in those coordinate systems or reference frames. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Registration of images may be implemented between the reference imaging system 102 and the IGRT delivery system 104 and/or between the data and/or images derived from the various modalities of the multimodal IGRT delivery system 104, including the low energy source(s) 110 and the high energy source 108 (and their associated detectors 112). In particular, referring back to apparatus 10, registration may be implemented between data and/or images derived from radiation sources 20, 30 and detectors 24, 34.

Dual-source system (e.g., kV-MV) imaging, including in the context of IGRT, can address and solve several problems and limitations of typical imaging systems used in these environments. Generally, combining a data acquisition from a kV subsystem and a data acquisition from a MV subsystem can yield various improvements. For example, in some embodiments kV projection data can be used to complete MV projection data and vice versa. In other embodiments, MV projection data can be used for ROI kV imaging. In yet other embodiments, data from both modalities can be used to complement each other. The methods can be significant for obese patient scans, ROI imaging, etc., for improved image quality (e.g., reduced x-ray scatter and thus enhanced contrast of soft tissues).

In one embodiment, for example, projection data corresponding to a targeted ROI acquired using a primary imaging system can be combined with additional projection data acquired using a secondary imaging system that correspond to regions outside of the scan FOV of the primary imaging system. In one embodiment, projection data from the secondary imaging system can then be used to estimate the missing or incomplete data outside the scan FOV of the primary imaging system, which is necessary for image reconstruction. For example, for an obese patient scan, an MV subsystem can be used to acquire the central region of the patient (which is laterally truncated) and a kV subsystem can be used to acquire the peripheral region of the patient. The kV projection data can then be used to help estimate the missing MV projection data for improved quality of image reconstruction.

Several other exemplary embodiments will be discussed in detail below. Each of these embodiments may use one or more exemplary scan configurations.

Figure 4:
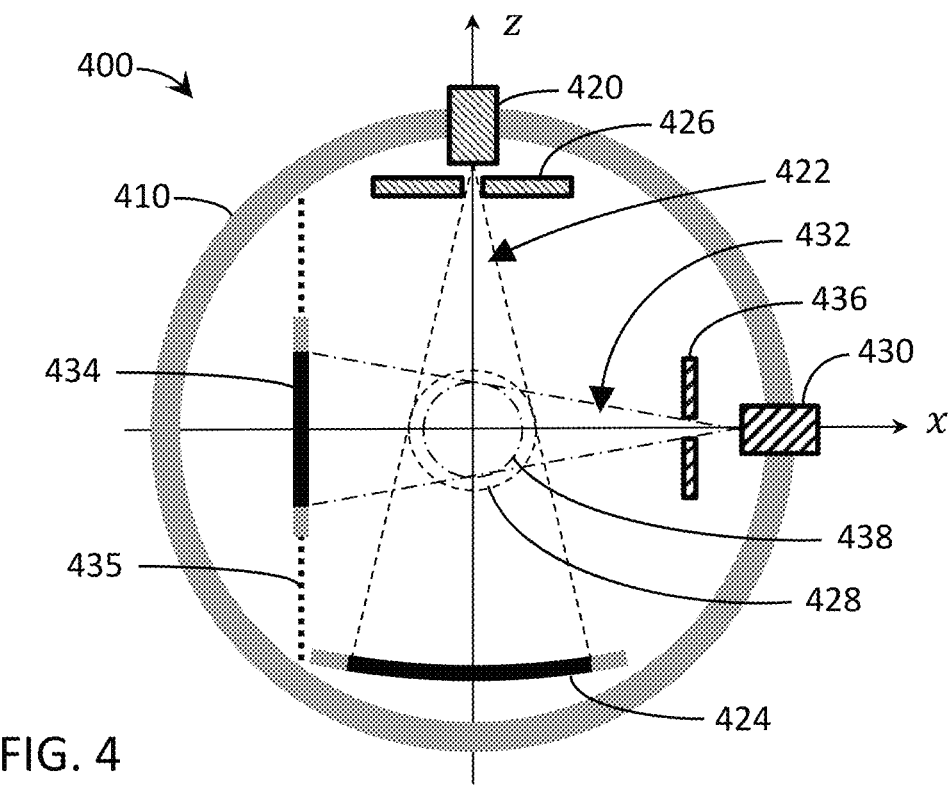
FIG. 4 shows an illustration of an exemplary multimodal scan configuration.

In one embodiment, FIG. 4 shows an illustration of an exemplary multimodal scan configuration 400. Looking into the front of the ring gantry 410, FIG. 4 shows a high energy radiation source 420 (e.g., MV) and a low energy radiation source 430 (e.g., kV) mounted to the ring gantry 410. Radiation sources 420, 430 are shown mounted orthogonal to each other, but other embodiments can include other angular relationships and additional radiation sources and/or detectors. High energy radiation source 420 is shown projecting radiation through a collimator or beamformer 426 to create radiation beam 422 projecting onto a portion of detector 424. In this configuration, high energy radiation source 420 has transaxial FOV 428. Low energy radiation source 430 is shown projecting radiation through a beamformer 436 to create radiation beam 432 projecting onto a portion of detector 434. In this configuration, low energy radiation source 430 has transaxial FOV 438. Detector 434 is shown centered within its range 435. In this manner, the radiation sources 420, 430 will project radiation through an overlapping transaxial FOV. In this embodiment, the multimodal scan configuration 400 shows the high energy FOV 428 with a larger transaxial FOV than the low energy FOV 438.

Figure 5:
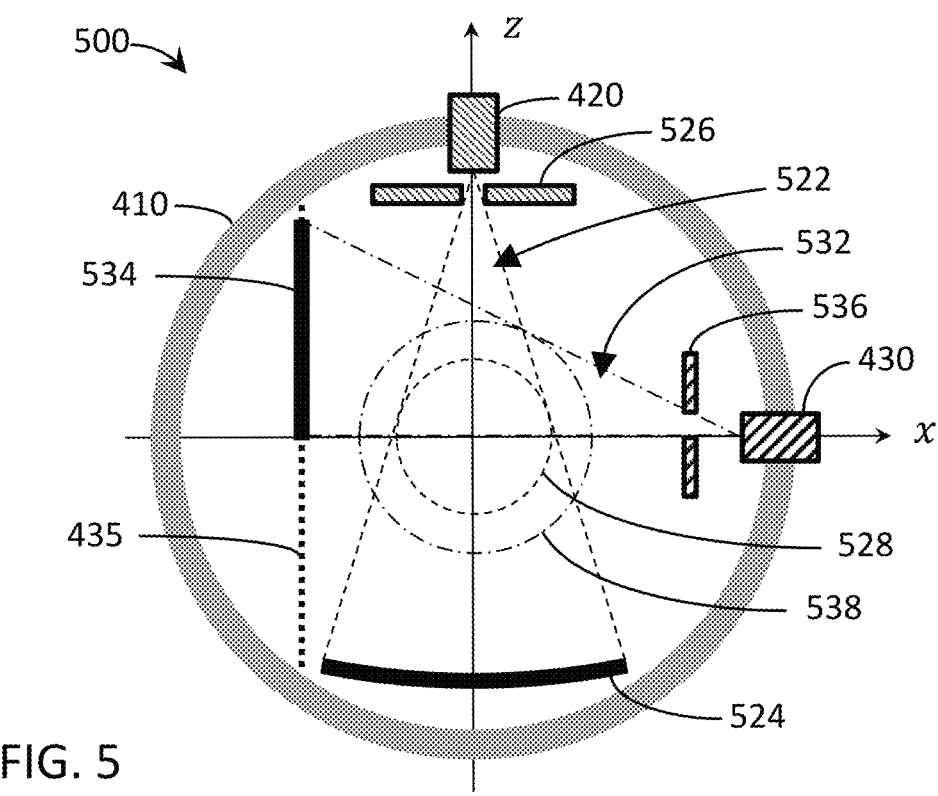
FIG. 5 shows an illustration of another exemplary multimodal scan configuration.

In another embodiment, FIG. 5 shows an illustration of another exemplary multimodal scan configuration 500. Looking into the front of the ring gantry 410, FIG. 5 also shows the high energy radiation source 420 and the low energy radiation source 430 mounted orthogonally to the ring gantry 410. High energy radiation source 420 is shown projecting radiation through a beamformer 526 to create radiation beam 522 projecting onto detector 524. In this configuration, high energy radiation source 420 has transaxial FOV 528. Low energy radiation source 430 is shown projecting radiation through a beamformer 536 to create radiation beam 532 projecting onto offset detector 534. In this configuration, low energy radiation source 430 has transaxial FOV 538 with at least 180 degrees of rotation.

In this manner, the radiation sources 420, 430 will also project radiation through an overlapping transaxial FOV. In this embodiment, the multimodal scan configuration 500 shows the low energy FOV 538 with a larger transaxial FOV than the high energy FOV 528.

In these and other embodiments, multimodal systems can consist of two or more sub-imaging systems, for example, MV (e.g., MVCT) and kV (e.g., kVCT). The MV imaging system consists of a MV radiation source (e.g., 420) and a MV radiation detector (e.g., 424) and the kV imaging system consists of a kV radiation source (e.g., 430) and a kV radiation detector (e.g., 434). Respective beamformers (e.g., 426 and/or 436) may also be included in the subsystems. The MV and kV imaging systems are not necessarily co-planar. For example, a small longitudinal distance between the two subsystems may be allowed. The kV system can be about 90 degrees apart from the MV system.

In some embodiments, the MV detector can be fixed, resulting in a fixed scan FOV, whereas the kV detector is translatable along a line in the gantry plane such that the corresponding scan FOV of the kV imaging system is flexible, as shown above in FIGS. 4-5. Such a flexible scan FOV can be implemented with an actuatable beamformer to avoid unnecessary x-ray dose to the patient. The systems may also include other pre- and post-patient filters.

Various factors, including, for example, beamformer configurations, radiation source angles, detector positions, etc. may be used to control the respective FOVs (e.g., transaxial and axial) of the radiation sources. In some embodiments, the radiation sources 420, 430 may be physically offset in the longitudinal direction (along the y-axis) and may scan the patient at different times (temporally offset).

Figure 6:
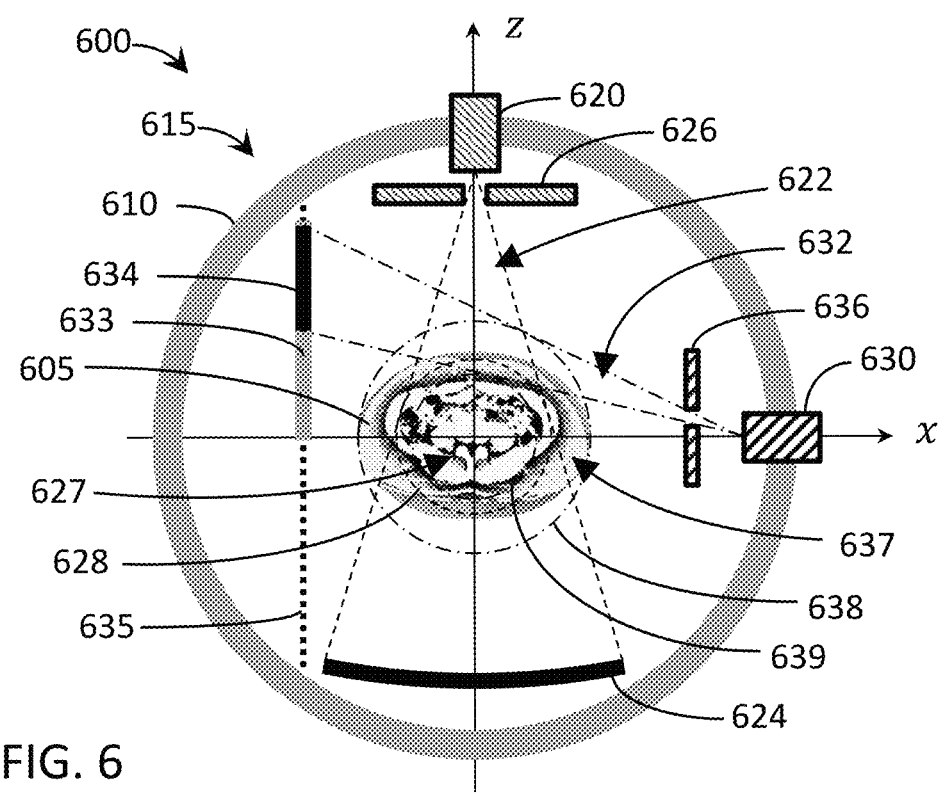
FIG. 6 shows an illustration of an exemplary multimodal scan configuration projecting through an exemplary large patient in a transaxial plane.

In one embodiment, FIG. 6 shows an illustration of an exemplary multimodal scan configuration 600 projecting through an exemplary large patient 605 in a transaxial plane 615. This embodiment may be applicable to imaging large patients that extend beyond a MV system transaxial FOV and/or to reduce the x-ray dose to the patient. Looking into the front of the ring gantry 610, FIG. 6 shows a MV radiation source 620 and a kV radiation source 630 mounted orthogonally to the ring gantry 610.

The MV radiation source 620 is shown projecting radiation through a beamformer 626 to create radiation beam 622 projecting onto detector 624. In this configuration, the MV radiation source 620 has a transaxial FOV within central region 627 bounded by 628.

The kV radiation source 630 is shown projecting radiation through a beamformer 636 to create radiation beam 632 projecting onto offset detector 634. Flat panel detector 634 is shown offset within its range 635 and with unexposed area 633 (due to beamformer 636). In this configuration, the kV radiation source 630 has a transaxial FOV in a peripheral region 637 bounded by 638 and 639 with at least 180 degrees of rotation.

In this manner, the radiation sources 620, 630 will project radiation through an adjacent or overlapping transaxial FOV (i.e., where the central region 627 and the peripheral region 637 overlap). In some embodiments, a bowtie filter (not shown) may be utilized to enable a larger dynamic range of the detector 634.

Figure 7:
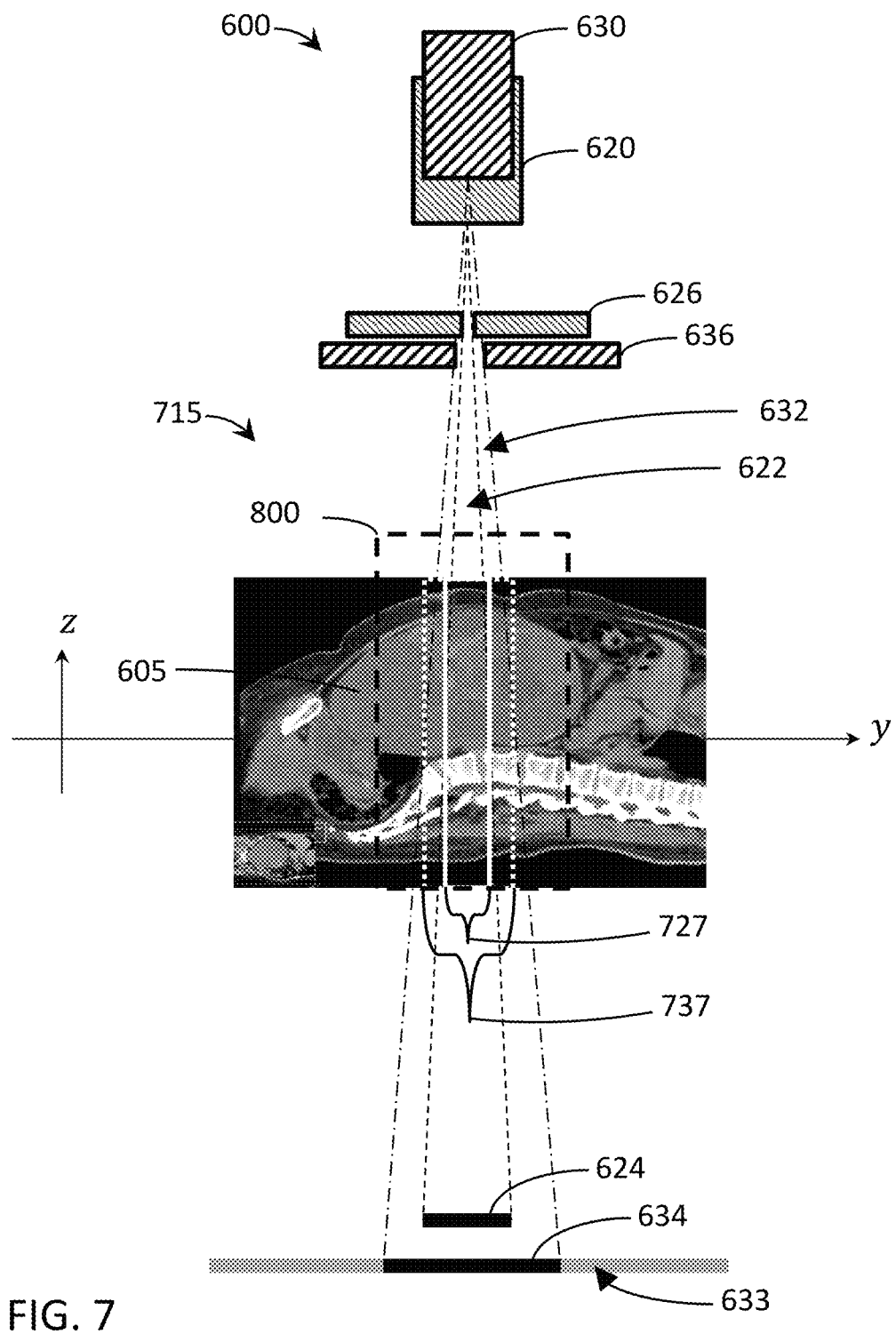
FIG. 7 shows another illustration of the exemplary multimodal scan configuration shown in FIG. 6 projecting through the exemplary large patient in an axial plane with a superimposed view of the radiation systems.

FIG. 7 shows another illustration of the exemplary multimodal scan configuration 600 projecting through the exemplary large patient 605 in an axial (longitudinal) plane 715 with a superimposed view of the radiation systems. Looking into the side of the ring gantry (not shown), FIG. 7 shows the position of the MV radiation source 620 and the kV radiation source 630 rotated and superimposed in the same axial plane 715. Radiation sources 620, 630 are not necessarily mounted in the same plane and are not typically mounted against each other (e.g., they may be mounted to the gantry system 90 degrees apart), but are shown superimposed in FIG. 7 to show an exemplary overlap of their respective views and features. Other embodiments can include other angular relationships and additional radiation sources and/or detectors.

The MV radiation source 620 is shown projecting radiation through beamformer 626 to create radiation beam 622 projecting onto detector 624. In this configuration, the MV radiation source 620 has axial FOV 727. The kV radiation source 630 is shown projecting radiation through beamformer 636 to create radiation beam 632 projecting onto a portion of detector 634. In this configuration, the kV radiation source 630 has axial FOV 737. Detector 634 is shown with shadowed region 633, which is blocked from direct radiation by beamformer 636. Detectors may have shadowed regions in axial and/or transaxial directions. In this manner, the radiation sources 620, 630 will project radiation through an overlapping axial FOV.

Figure 8:
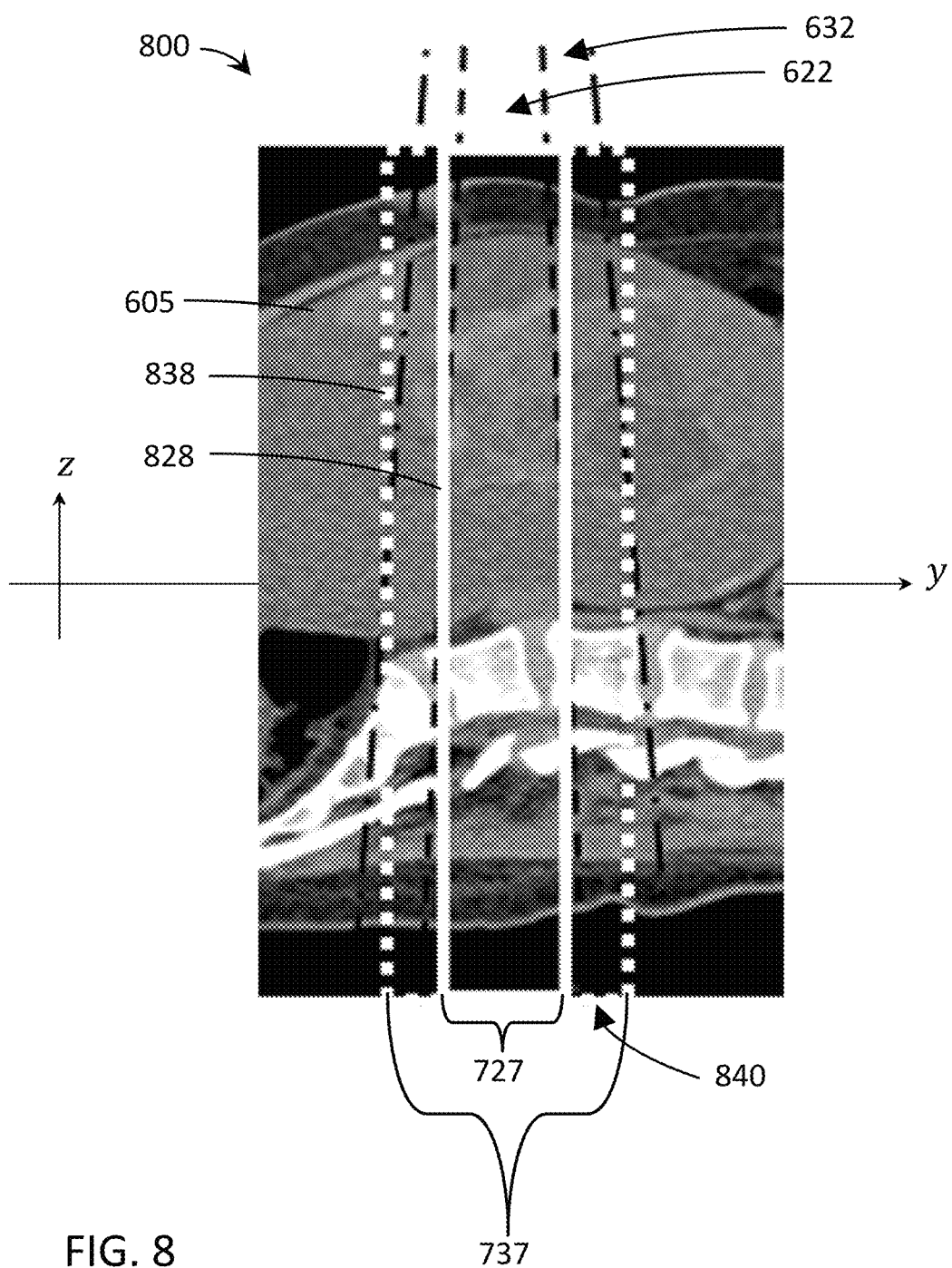
FIG. 8 shows an illustration of a zoomed-in portion of the target shown in FIG. 7.

FIG. 8 shows a zoomed-in portion 800 of the axial plane 715 shown in FIG. 7. Radiation beams 622, 632 are shown passing through patient 605. The MV system axial FOV region 727 is bounded by 828 and the kV system axial FOV region 737 is bounded by 838, providing overlapping imaging data. Here, the kV system axial FOV 737 provides imaging data beyond the MV system axial FOV 727, shown as region 840.

As mentioned above, this configuration can be designed for large field-of-view (LFOV) MV imaging, including for imaging large or obese patients. It can use both MV and kV subsystems of a multimodal system. In one embodiment, as shown in the transaxial plane 615 of FIG. 6, the MV system is used to acquire projection data corresponding to the central region 627 of the scanned patient 605. The MV projection data are truncated due to the large size of the patient 605 and limited transaxial FOV 628 of the MV detector 624. The kV system is used to acquire projection data corresponding to the peripheral region 637 of the scanned patient 605. The kV projection data are also truncated inside of boundary 639, which is within the central region 627 boundary 628. It is required that there is overlap between the kV and MV projection data at the same angular position (which may correspond to different timings). The design of the two subsystems is also shown in the axial (longitudinal) direction in FIGS. 7-8.

The following flow charts and block diagrams illustrate exemplary configurations and methodologies associated with the multimodal radiation systems described above. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 9:
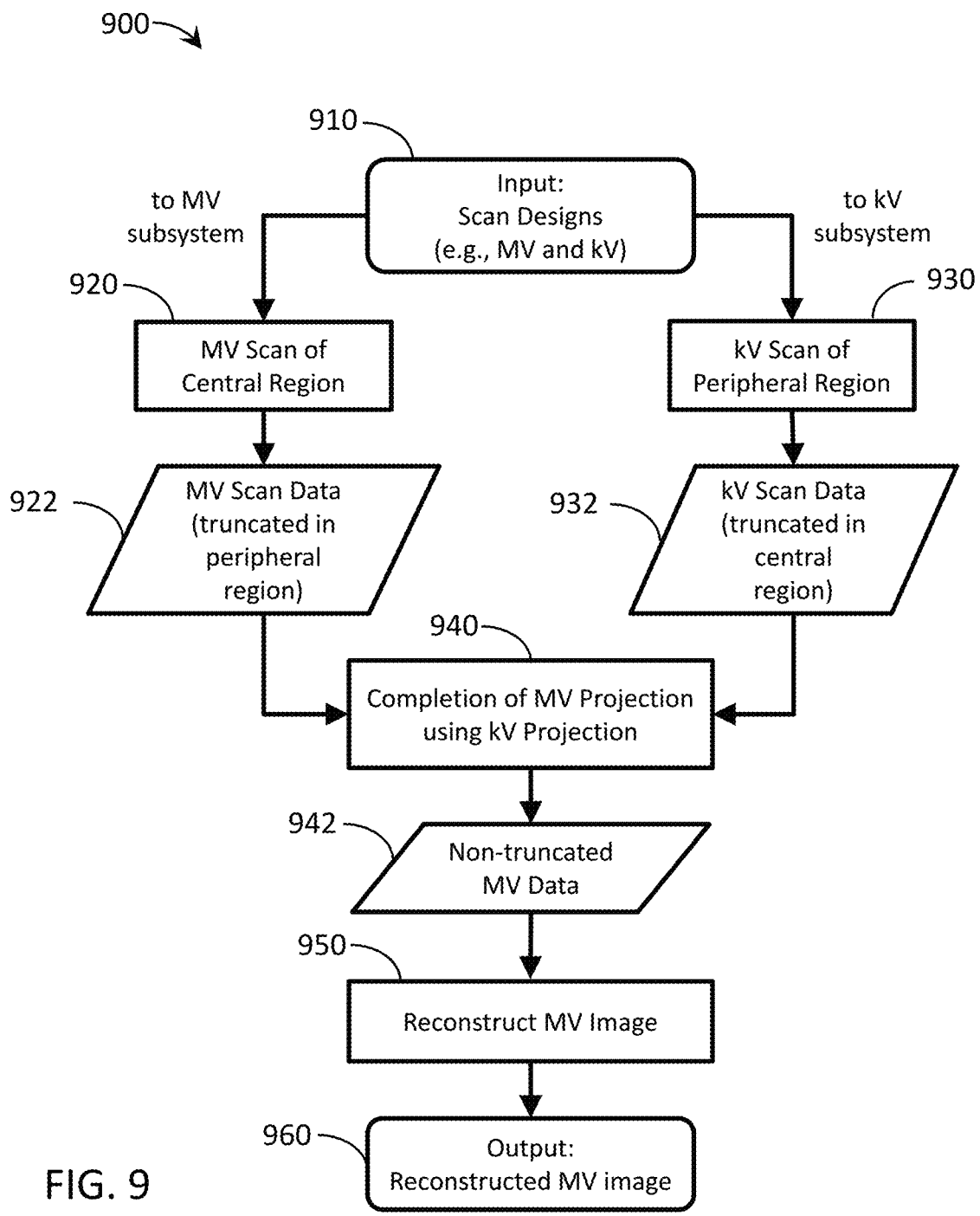
FIG. 9 is a flow chart depicting an exemplary method of combining scan data from multiple radiation modalities to approximate missing MV projection data using kV projection data.

FIG. 9 is a flow chart depicting an exemplary method 900 of combining scan data from multiple radiation modalities, such as those described above, to approximate missing MV projection data in a peripheral region using kV projection data. At step 910, the method 900 determines a scan configuration, including scan designs for each modality of the multimodal system. A MV scan of a central region is executed at step 920. A kV scan of a peripheral region is executed at step 930. As described above, the respective scans produce MV scan data 922 (truncated in the peripheral region) and kV scan data 932 (truncated in the central region). Next, at step 940, the method 900 makes use of or combines the kV scan data 932 to complete the MV scan data 922 to form a complete MV projection or non-truncated MV data 942. Then, at step 950, the method 900 processes the non-truncated MV data 942, for example, to reconstruct a MV image. At step 960, the reconstructed MV image can be output.

In another embodiment, FIG. 10 shows an illustration of an exemplary multimodal scan configuration 1000 projecting through an exemplary patient 1005 in a transaxial plane 1015. This embodiment may be applicable to imaging to reduce the x-ray dose to the patient, reduce x-ray scatter, and/or improve kV image quality, especially, for example, in terms of soft tissue visibility. Looking into the front of the ring gantry 1010, FIG. 10 shows a MV radiation source 1020 and a kV radiation source 1030 mounted orthogonally to the ring gantry 1010.

The MV radiation source 1020 is shown projecting radiation through a beamformer 1026 to create radiation beam 1022 projecting onto detector 1024. Detector 1024 is shown with shadowed region 1023, which is blocked from direct radiation by beamformer 1026. In this configuration, the MV radiation source 1020 has a transaxial FOV within intermediate region 1027 bounded by 1028 and 1029. FIG. 11 shows an illustration of the MV subsystem 1100 of exemplary multimodal scan configuration 1000.

The kV radiation source 1030 is shown projecting radiation through a beamformer 1036 with two apertures to create radiation beam(s) 1032 projecting onto offset detector portions 1034 and 1044. The flat panel detector is shown offset within its range 1035 and with unexposed area 1033 (due to beamformer 1036). In this configuration, the kV radiation source 1030 has a transaxial FOV in a peripheral region 1037 bounded by 1038 and 1039 with at least 180 degrees of rotation relative to the point of interest and in a central region 1047 bounded by 1048. In some embodiments, the central region 1047 may include a target region of the patient. FIG. 12 shows an illustration of the kV subsystem 1200 of exemplary multimodal scan configuration 1000. While this embodiment includes both the kV central region 1047 and the kV peripheral region, other embodiments need not include both. For example, another embodiment includes only the central region 1047 (with one kV aperture).

In this manner, the radiation sources 1020, 1030 will project radiation through an adjacent or overlapping transaxial FOV (i.e., where the MV intermediate region 1027 overlaps with the kV peripheral region 1037 and the kV central region 1047). FIG. 13 shows an illustration of the MV FOV intermediate region 1027 and the kV FOV peripheral region 1037 and central region 1047 created by the multimodal scan configuration 1000 in a superimposed view 1300. In particular, the MV FOV intermediate region 1027 and the kV FOV central region 1047 overlap at region 1310 (shaded) and the MV FOV intermediate region 1027 and the kV FOV peripheral region 1037 overlap at region 1312 (shaded).

As mentioned above, this configuration can be designed for kV region-of-interest (ROI) imaging, including to reduce the x-ray dose, reduce x-ray scatter, and/or improve kV image quality. In other embodiments, a similar configuration can be used for MV ROI imaging. It can use both MV and kV subsystems of a multimodal system. In one embodiment, as shown in the transaxial plane 1015 of FIGS. 10 and 12, the kV subsystem 1200 provides two scan FOVs 1037, 1047. The central region 1047 is located at the center and the peripheral region 1037 is a donut shape located at the periphery. The central region 1047 can be the target ROI for the patient, whereas the peripheral region 1037 can be for auxiliary purposes. The two scan FOVs 1037, 1047 are disconnected and thus are missing projection data between the two scan FOVs 1037, 1047 that are needed for exact image reconstruction. In one embodiment, an estimate of those missing kV data can be based on the available kV projection data via, e.g., interpolation. The kV projection data of the peripheral region 1037 is important for this estimation of missing data because it will provide the range information of the patient. However, as mentioned above, in one more simplified ROI embodiment, the peripheral region 1037 is not used.

In this embodiment, the kV beamformer 1036 portion corresponding to the peripheral scan FOV 1037 may be adaptive to the patient shape to save dose (and may involve usage of prior CT data). The MV projection data may or may not be needed, depending on the application. In one embodiment, as shown in the transaxial plane 1015 of FIGS. 10 and 11, the MV subsystem 1100 can provide projection data in a scan FOV 1027 that can compensate or complement the kV scan FOVs 1037, 1047, such that it will provide information for better kV data completion. Note that a bowtie filter may be involved to enable larger dynamic range of the flat panel detector.

Figure 14:
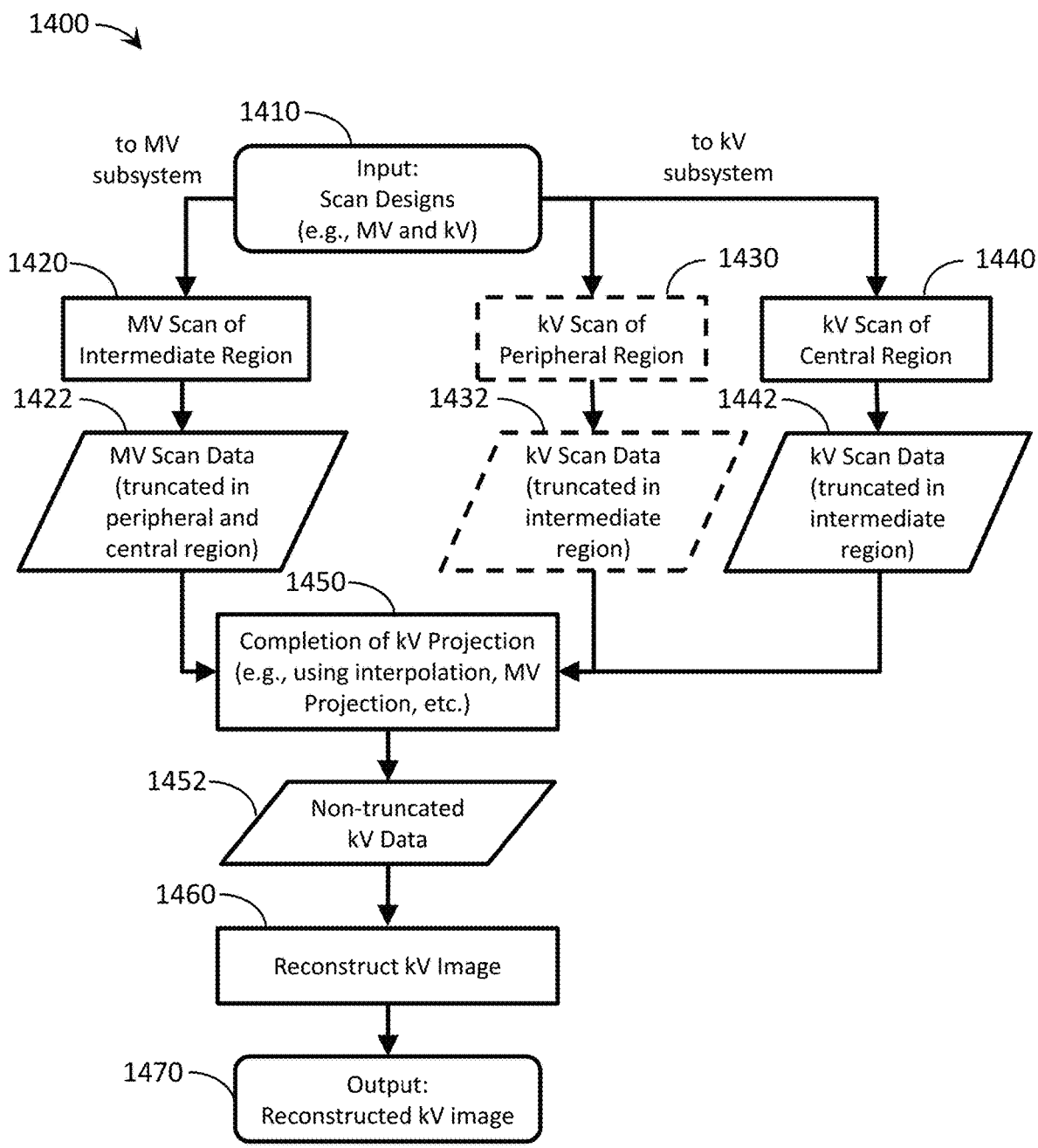
FIG. 14 is a flow chart depicting an exemplary method of combining scan data from multiple radiation modalities to approximate missing kV projection data using MV projection data.

FIG. 14 is a flow chart depicting an exemplary method 1400 of combining scan data from multiple radiation modalities, such as those described above, to approximate missing kV projection data in an intermediate region using MV projection data. At step 1410, the method 1400 determines a scan configuration, including scan designs for each modality of the multimodal system. A MV scan of an intermediate region is executed at step 1420. A kV scan of a peripheral region is executed at step 1430 (if embodiment with peripheral region included). A kV scan of a central region is executed at step 1440. As described above, the respective scans produce MV intermediate scan data 1422 (truncated in the peripheral and central region), kV peripheral scan data 1432 (truncated in the intermediate region), and kV central scan data 1442 (truncated in the intermediate region). KV projection data is missing between the kV peripheral and central regions. Next, at step 1450, the method 1500 makes use of or combines the MV scan data 1422 to complete the kV scan data 1432, 1442 to form a complete kV projection or non-truncated kV data 1452. Step 1450 may also include interpolation of the kV scan data 1432, 1442 (e.g., optimized with the MV scan data 1422), prior CT data (pCT) if available, etc., in addition to or instead of the use of the MV scan data 1422. Registration, rebinning, and/or other processes (e.g., attenuation constant normalization, scatter correction, scaling, etc.) may also be involved with step 1450. In embodiments without the kV peripheral scan 1430, kV data 1432 is not available and is not used. Then, at step 1460, the method 1400 processes the non-truncated kV data 1452, for example, to reconstruct a kV image. At step 1470, the reconstructed kV image can be output.

In an embodiment where MV scan data 1422 (e.g., via step 1420) and/or pCT data are available, use of those data can be made to improve the estimation of the missing kV data at step 1450. Usage of the estimated data can be mainly for the global filtration operators involved in the reconstruction. In some embodiments, it may be recommended to only perform image reconstruction in the ROI region.

As mentioned above, in some embodiments, the beamformer 1036 portion corresponding to the kV peripheral scan FOV 1037 can be adaptive to follow the patient shape to further reduce patient dose. The rough patient shape can be estimated, for example, by pCT, scout views, adaptive feedback from projections, etc. In some embodiments, the beamformer 1036 portion corresponding to the central scan FOV 1047 can be adaptive to a non-central ROI to provide flexibility of ROI selection. Other embodiments may employ a combination of both adaptive techniques.

The MV subsystem 1100 can be used to provide a scatter-and/or dose-reduced scan 1420 with a scan FOV 1027 that is located between the kV peripheral and central scan FOVs 1037, 1047, to provide more accurate estimation of the missing kV projection data. This process (e.g., at step 1450) may involve registration, rebinning, and/or mapping between the MV and kV data. Available pCT data can be used to improve the estimation accuracy of the missing kV projection data. This process (e.g., at step 1450) may involve registration, rebinning, and/or mapping between the pCT and the kV data.

Figure 15:
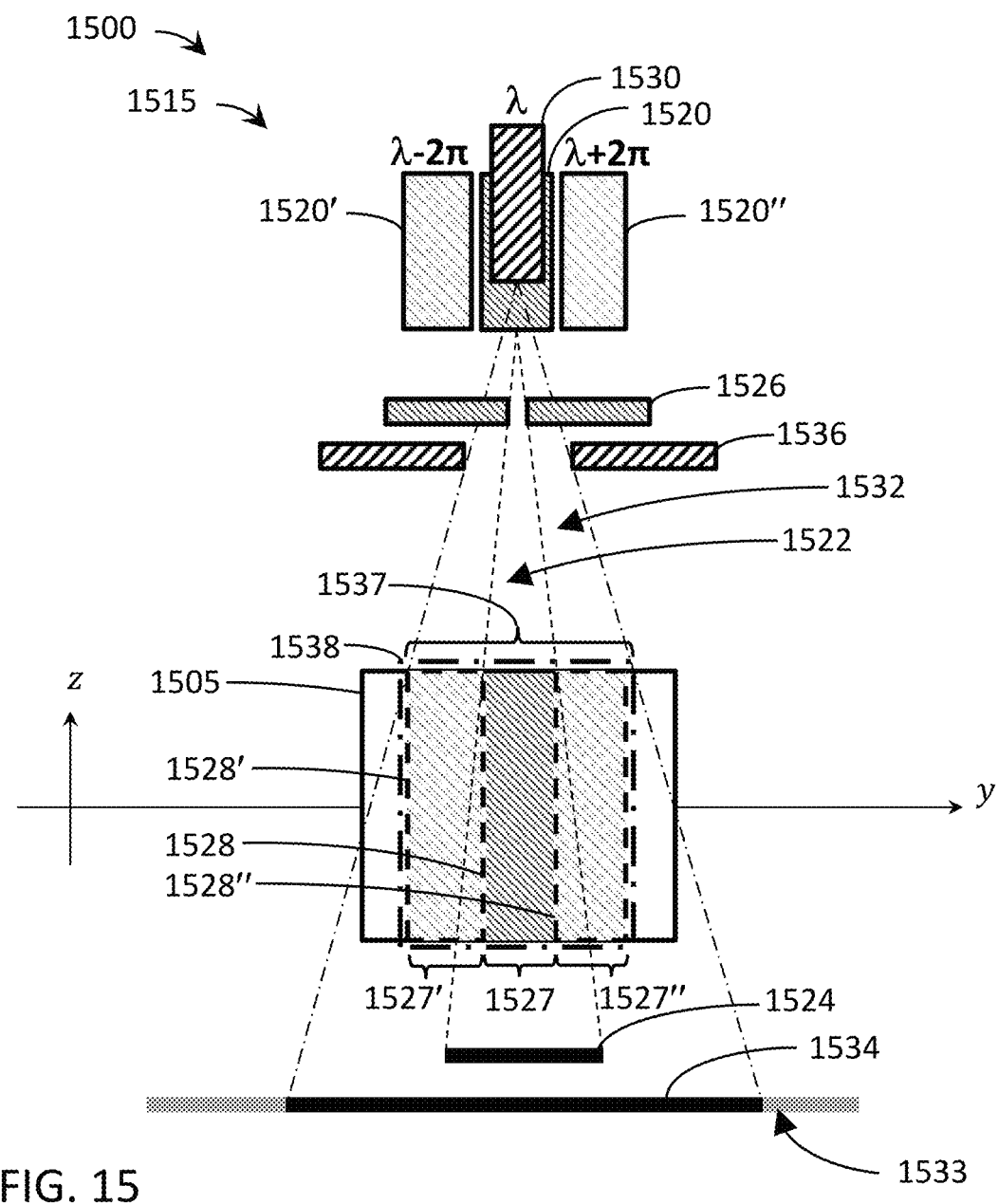
FIG. 15 shows an illustration of an exemplary multimodal scan configuration projecting through an exemplary patient in an axial plane with a superimposed view of the radiation systems.

In another embodiment, FIG. 15 shows an illustration of an exemplary multimodal scan configuration 1500 projecting through an exemplary patient 1505 in an axial (longitudinal) plane 1515 with a superimposed view of the radiation systems. This embodiment may be applicable for scalable FOV (SFOV) dual-energy imaging, which provides a variety of options, including, for example, SFOV configurations for IGRT. This embodiment is an example of both scalable transaxial FOV and scalable axial FOV. Generally, a wider kV axial FOV can allow for better modeling of the MV projections over finite cell dimensions. This may be important for a wide single-row MV detector, improving slice thickness of the multimodal image. Looking into the side of the ring gantry (not shown), FIG. 15 shows the position of the MV radiation source 1520 and the kV radiation source 1530 rotated and superimposed in the same axial plane 1515. Radiation sources 1520, 1530 are not necessarily mounted in the same plane and are not typically mounted against each other (e.g., they may be mounted to the gantry 90 degrees apart), but are shown superimposed in FIG. 15 to show an exemplary overlap of their respective views and features. Other embodiments can include other angular relationships and additional radiation sources and/or detectors.

The MV radiation source 1520 is shown projecting radiation through beamformer 1526 to create radiation beam 1522 projecting onto detector 1524. In this configuration, the MV radiation source 1520 has axial FOV 1527 bounded by 1528 at an angular position λ. During a prior rotation, the MV radiation source, designated as 1520', has a neighboring axial FOV 1527' bounded by 1528' at an angular position λ−2π radians (a difference of one complete revolution). During a subsequent rotation, the MV radiation source, designated as 1520", has a neighboring axial FOV 1527" bounded by 1528" at an angular position λ+2π radians. Prime notation (') is used to indicate that a component of the system has moved or changed in comparison to its non-prime or other prime form or position. For example, "1520," "1520'," and "1520"," all refer to the MV radiation source 1520, but at different angular positions.

The kV radiation source 1530 is shown projecting radiation through beamformer 1536 to create radiation beam 1532 projecting onto a portion of detector 1534. In this configuration, the kV radiation source 1530 has axial FOV 1537 bounded by 1538. Detector 1534 is shown with shadowed region 1533, which is blocked from direct radiation by beamformer 1536. Detectors may have shadowed regions in axial and/or transaxial directions.

In this manner, the radiation sources 1520, 1530 will project radiation through an overlapping axial FOV (e.g., axial MV FOVs 1527'+1527+1527"=axial kV FOV 1537). In this embodiment, MV radiation source 1520 requires three revolutions whereas the kV radiation source requires one revolution to accumulate the same axial FOV width. As mentioned above, the superimposed view of the radiation sources 1520, 1530 in FIG. 15 is only for illustration purposes. The kV and MV subsystems can arrive at the illustrated angular position at different timings. Also, at this angular position, they may have different longitudinal positions. The kV subsystem provides a much larger longitudinal scan FOV 1537 than the MV subsystem FOV 1527, which provides additional time for the kV subsystem to complete a larger in-plane (transaxial) scan FOV, for example, during multiple rotations, as discussed below.

FIGS. 16 and 17 show illustrations of the exemplary kV radiation source 1530 during the multimodal scan configuration 1500 projecting through the exemplary patient 1505 in a transaxial plane 1615 during different rotations.

Looking into the front of the ring gantry 1610, FIG. 16 shows kV radiation source 1530 mounted to the ring gantry 1610 during rotation A. The kV radiation source 1530 is shown projecting radiation through the beamformer 1536 to create radiation beam 1532 projecting onto offset detector 1534. Flat panel detector 1534 is shown offset within its range 1635 and with unexposed area 1533 (due to beamformer 1536). Detectors may have shadowed regions in axial and/or transaxial directions. In this configuration during rotation A, the kV radiation source 1530 has a transaxial FOV in a peripheral region 1537 bounded by 1538 and 1539 with at least 360 degrees of rotation.

FIG. 17 shows kV radiation source 1530 mounted to the ring gantry 1610 during rotation B. The kV radiation source 1530 is shown projecting radiation through the beamformer 1536' to create radiation beam 1532' projecting onto offset detector 1534'. Flat panel detector 1534' is shown centered within its range 1635 and with unexposed area 1533' (due to beamformer 1536'). In this configuration during rotation B, the kV radiation source 1530 has a transaxial FOV in a central region 1537' bounded by 1538'. The central region 1537' may correspond to a target ROI of the patient 1505. In embodiments where the target ROI is away from the isocenter, dynamic collimation of the beamformer 1536' will be required.

In this manner, radiation source 1530 will project radiation through adjacent or overlapping transaxial FOVs (i.e., where the peripheral region 1537 and the central region 1537' overlap). The peripheral kV scan FOV 1537 (donut shaped) corresponds to an off-centered detector position 1534, whereas the central kV scan FOV 1537' (disk shaped) corresponds to a centered detector position 1534'. The union of the two kV scan FOVs 1537, 1537' results in a complete and large kV scan FOV. In this embodiment, kV transaxial FOVs 1537, 1537', during rotations A and B, respectively, overlap at region 1810 as shown in the superimposed view 1800 of FIG. 18. In different embodiments, the kV radiation source 1530 can be on or off as the beamformer 1536 transitions between projecting to the peripheral region 1537 and the central region 1537' in the transaxial plane 1615 of the patient 1505.

The transaxial views 1615, 1615' shown in FIGS. 16 and 17, during rotations A and B, can coincide with the axial view 1515 at the various angular positions (λ−2π, λ, and λ+2π) shown in FIG. 15. FOVs have temporally coincident axial and transaxial characteristics that are shown separately in the different views of the figures. For example, the kV radiation source 1530 FOV 1537 encompasses the axial characteristics shown in FIG. 15 and the transaxial characteristics shown in FIGS. 16 and 17 at the same time, during various revolutions.

In this embodiment, the kV detector 1534 can be much larger than the MV detector 1524 in the longitudinal direction (e.g., as shown in FIG. 15). By using a much larger longitudinal kV scan FOV 1537 than the MV scan FOV 1527, the kV subsystem has more time to provide a larger in-plane (transaxial) scan FOV.

In some embodiments, a key design parameter can be how much larger should the illuminated kV detector 1534 be than the smaller MV detector 1524. For example, let H be the MV detector width at the iso-center. Let sH be the illuminated kV detector width at the iso-center, with s being a scalar larger than 1. In one embodiment, the criteria to determine the value of s is such that: at any rotation angle, any point that 1) is inside the target in-plane scan FOV; and 2) is visible by the MV radiation source 1520, should be visible by the kV radiation source 1530 at any azimuth angle at least once. This requirement can be achieved by a combination of moving the kV detector 1534 and use of a dynamic beamformer 1536. In this embodiment, it is also important to make sure that the movement of the kV detector 1534 and the kV beamformer 1536 are both continuous.

FIGS. 15-18 demonstrate an exemplary embodiment that satisfies this requirement. In this embodiment, the axial (longitudinal) kV FOV 1537 is about 3 times larger than the axial MV FOV 1527. At one rotation angle ($\lambda$), as shown in FIG. 15, the current MV illuminated portion of the object (indicated by the boundary 1528) is visible at the same azimuth angle by the previous ($\lambda-2\pi$), current ($\lambda$), and next rotations ($\lambda+2\pi$), shown as 1528', 1528, and 1528'', respectively. During these three rotations, one rotation (e.g., Rotation A as shown in FIG. 16) is dedicated to the peripheral kV scan with kV FOV 1537, and another rotation (e.g., Rotation B as shown in FIG. 17) is dedicated to the central kV scan with kV FOV 1537'. The (left) edge of one rotation can be used to make sure that the transition between the peripheral region 1537 and the central region 1537' is smooth. This configuration 1500 can be used to provide both MV and kV projection data in the same ROI, enabling dual energy imaging for the ROI.

In this embodiment, the two kV scan FOVs 1537, 1537' shown in FIGS. 16-18 may not be acquired consecutively. A period of time can be required to translate the detector from one position to another. However, as mentioned above, since the kV subsystem provides a much larger axial FOV 1537 than the MV subsystem FOV 1527, additional time is available for the kV subsystem to complete a larger transaxial scan FOV during the same time period required for the full axial MV scan. For example, in one embodiment: step 1—first full rotation (rotation index 0→1.0), a first kV scan full rotation (e.g., Rotation B shown in FIG. 17 with the kV beamformer focusing on the central transaxial FOV) can coincide with a first MV scan full rotation (e.g., $\lambda-2\pi$ rotation shown in FIG. 15); step 2—the next half rotation (rotation index 1.0→1.5), translating the kV beamformer and/or the kV detector to the peripheral transaxial region can coincide with a first half of a second MV scan rotation (e.g., first half of $\lambda$ rotation shown in FIG. 15); step 3—the next full rotation (rotation index 1.5→2.5), a second kV scan full rotation (e.g., Rotation A shown in FIG. 16 with the kV beamformer focusing on the peripheral transaxial FOV) can coincide with a second half of the second MV scan rotation (e.g., second half of $\lambda$ rotation shown in FIG. 15) and a first half of a third MV scan rotation (e.g., first half of $\lambda+2\pi$ rotation shown in FIG. 15); step 4—the next half rotation (rotation index 2.5→3.0), translating the kV beamformer and/or the kV detector back to the central transaxial region can coincide with a second half of the third MV scan rotation (e.g., second half of $\lambda+2\pi$ rotation shown in FIG. 15). These four steps can be repeated as a cycle. In this manner, complete axial and transaxial coverage can be achieved from dual energy sources 1520, 1530 during an overlapping time period (e.g., during three full rotations). As discussed above, the timing of the kV and MV scans of the same region can be somewhat offset due to the mounted position of the radiation sources 1520, 1530 within the ring gantry 1610.

Figure 19:
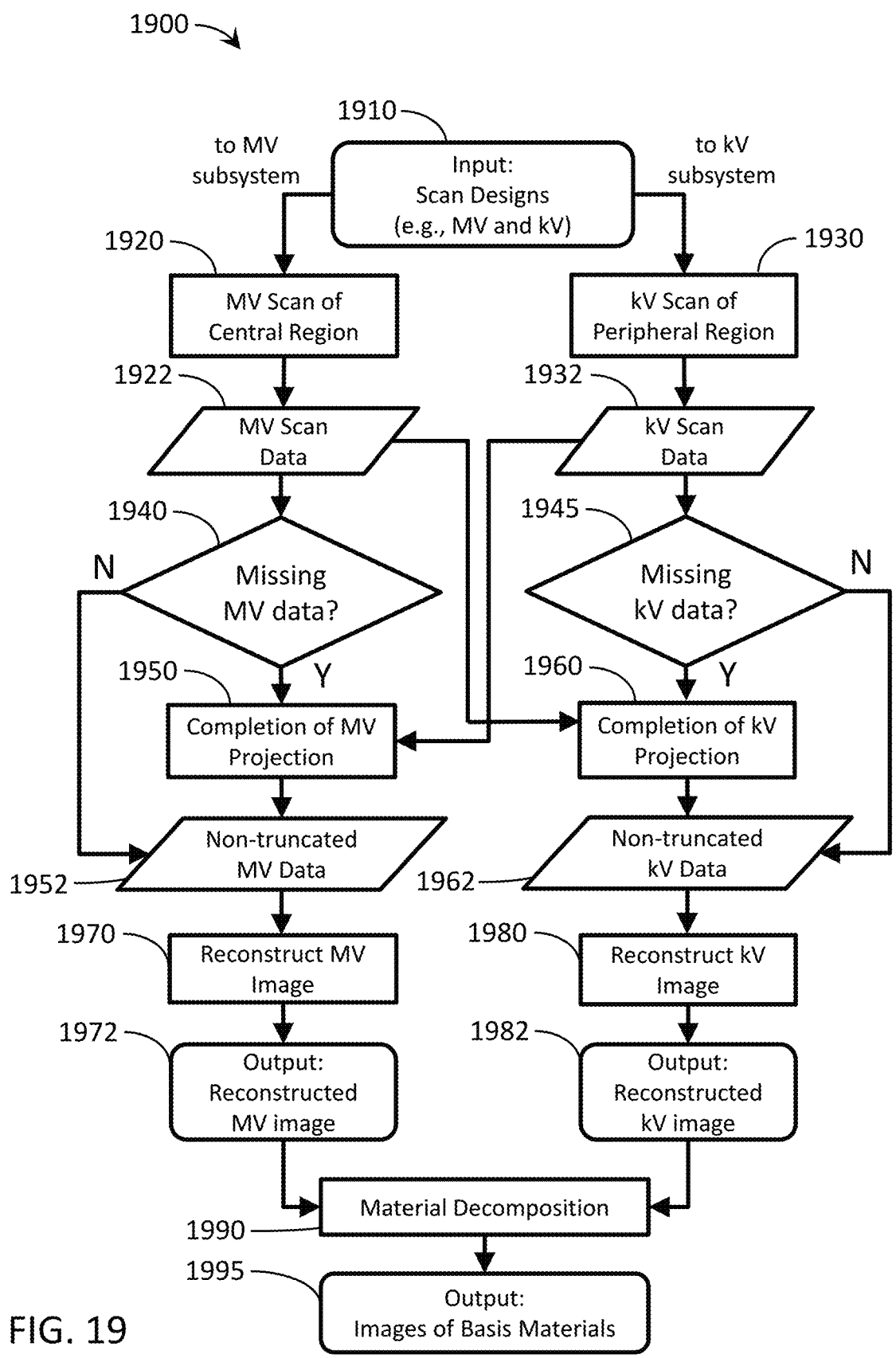
FIG. 19 is a flow chart depicting an exemplary method of combining scan data from multiple radiation modalities to approximate missing MV and/or kV projection data based on corresponding projection data from another modality.

FIG. 19 is a flow chart depicting an exemplary method 1900 of combining scan data from multiple radiation modalities, such as those described above, to approximate missing MV and/or kV projection data based on corresponding projection data from another modality. At step 1910, the method 1900 determines a scan configuration, including scan designs for each modality of the multimodal system. An exemplary MV scan of a central region is executed at step 1920. An exemplary kV scan of a peripheral region is executed at step 1930. As described above, the respective scans produce MV scan data 1922 (which may be truncated in the peripheral region) and kV scan data 1932 (which may be truncated in the central region).

At step 1940, the method 1900 determines whether the MV scan data 1922 is missing projection data. If yes, at step 1950, the method 1900 makes use of or combines the kV scan data 1932 to complete (e.g., estimate) the MV scan data 1922 to form a complete MV projection or non-truncated MV data 1952. If the MV scan data 1922 is not missing projection data, then the MV scan data 1922 is non-truncated MV data 1952. Then, at step 1970, the method 1900 processes the non-truncated MV data 1952, for example, to reconstruct a MV image. At step 1972, the reconstructed MV image can be output.

At step 1945, the method 1900 determines whether the kV scan data 1932 is missing projection data. If yes, at step 1960, the method 1900 makes use of or combines the MV scan data 1922 to complete (e.g., estimate) the kV scan data 1932 to form a complete kV projection or non-truncated kV data 1962. If the kV scan data 1932 is not missing projection data, then the kV scan data 1932 is non-truncated kV data 1962. Then, at step 1980, the method 1900 processes the non-truncated kV data 1962, for example, to reconstruct a kV image. At step 1982, the reconstructed kV image can be output. Data estimation during method steps 1950 and/or 1960 may involve registration, rebinning, mapping, and/or other processes as described above.

The method 1900 may also include step 1990, which makes use of a material decompensation engine to decompose the reconstructed images into basis materials. In one embodiment, the output image(s) is used for material decomposition within an overlapped region of the kV radiation source and the MV radiation source transaxial FOVs, resulting in basis material images. Then, at step 1995, images of basis materials can be output.

Although specific embodiments have been described, it should be appreciated that both transaxial and axial FOVs are scalable for each radiation source of a multimodal system in various combinations in other embodiments. (I.e., each modality of the multimodal system can have a scalable transaxial and/or axial FOV.) In some embodiments, the FOVs of the same and/or different modalities may be the same (e.g., transaxially and/or axially). In still further embodiments, the FOVs may be adjacent but not overlap, may have space between, may be banded such that one FOV is within the other without overlap, etc., and combinations thereof.

In some embodiments, one or more of the radiation sources may be used for sparse data, may utilize different resolutions, speeds, trajectories, frequencies, power levels, dosages, FOVs, etc. In any event, data from two or more radiation modalities can be used in combination to improve image quality, speed, dosing, workflow, treatment accuracy/precision, etc.

In various embodiments, the exemplary scan configurations (e.g., 400, 500, 600, 1000, 1500) and methods (e.g., 900, 1400, 1900) described above and those described below may be implemented using multimodal apparatus 10, including via radiation treatment environment 300.

In some embodiments, the scan configuration includes a helical scan trajectory. A helical fan-beam MV CT (MVCT) acquisition geometry can provide several advantages, including, for example, a wide transverse view (e.g., about 40 cm at the isocenter), capable of providing sufficient data for exact and stable image reconstruction, and decreased scatter fraction in projection images. These features can improve the quality of the reconstructed image over clinical state-of-the-art cone-beam MVCTs. In particular, for example, a source of these advantages is the fan-collimated MV treatment/imaging beam and the fact that the MV source and detectors are mounted on a continuously rotating slip-ring system that is capable of imaging from all directions, as described above. In operation, the system (e.g., apparatus 10) can image continuously over more than $2\pi$ radians, moving the source and detector in a helical trajectory with respect to a patient on a translating couch without stopping to unwind cabling or resorting to atypical imaging trajectories.

In various embodiments, the multimodal apparatus 10 can include N-tuple source and detector CT systems (where N sources and N or another number of detectors are positioned such that their respective projection image data can be acquired simultaneously) with sources providing multi-energetic (e.g., low energy and high energy) projection data. Combining the use of fan-beam imaging geometries (e.g., using helical scan trajectories) with simultaneous multi-energetic kV/MV imaging devices yields the advantages described herein. Typical existing systems are limited to cone-beam imaging geometries for either kV or MV sources individually, which have noticeable disadvantages over fan-beam imaging geometries, as described above.

In various embodiments, high energy MV fan-beam projections and low energy kV fan-beam or cone-beam projections can be acquired in simultaneous CT reconstructions. In some embodiments, the MV projections can be used as a priori information to amend artifacts of the kVCT, or used in a dual-energy CT reconstruction for quantitative imaging and material separation. Furthermore, multi leaf collimator (MLC)-modulated MV projection data is always available during treatment and may be leveraged in kVCT reconstructions concurrent with treatment delivery. Electron density images obtained from dual-energy reconstructions can be used in both online and offline dosimetry applications.

In some embodiments, the above methods can be executed simultaneously or in an interleaved manner based on a preferred workflow. For example, a multimodal scan can be performed and the resulting scan data utilized for two or more of the various features and benefits described above.

When the above apparatus and methods are used in the projection domain, it can be applied on each projection view, where each projection view is a planar image. Various embodiments can utilize different scan geometries, detector positioning (including offset detectors), and/or beamformer window shapes.

As is discussed above, aspects of the disclosed technology can be utilized in a radiotherapy device and methods that make use of multimodal radiation sources, including integrated low energy (e.g., kV) and high energy (e.g., MV) sources for use in conjunction with or as part of IGRT. In accordance with one embodiment, the image acquisition methodology can include or otherwise makes use of a helical source trajectory (e.g., a continuous source rotation about a central axis together with longitudinal movement of a patient support through a gantry bore) or a circular scan, together with fast slip ring rotation, for example, to provide kV CT imaging on a radiation therapy delivery platform.

In some embodiments, it will be appreciated that any potential increased scan time associated with multiple beam rotations to complete a volume image can be mitigated or otherwise offset by high kV frame rates, high gantry rates, and/or sparse data reconstruction techniques. It will be further appreciated that the above-described provision of a selectively controllable collimator/beamformer allows for a system where a user can trade off or otherwise vary image acquisition time versus image quality, depending on the specific application and/or clinical need. It also will be appreciated that the radiotherapy delivery device can be controlled to provide half- or single-rotation cone beam CT scans (with potential reduced image quality due to scatter) with fast image acquisition time (e.g., for motion tracking), as well as circular or continuous helical acquisition with a narrow/slit fan beam with longer acquisition time, but increased image quality due to reduced scatter. One or more optimization processes are also applicable to all of the above embodiments to determine scan designs, determine beam positioning, determine readout range, estimate scatter, etc.

Figure 20:
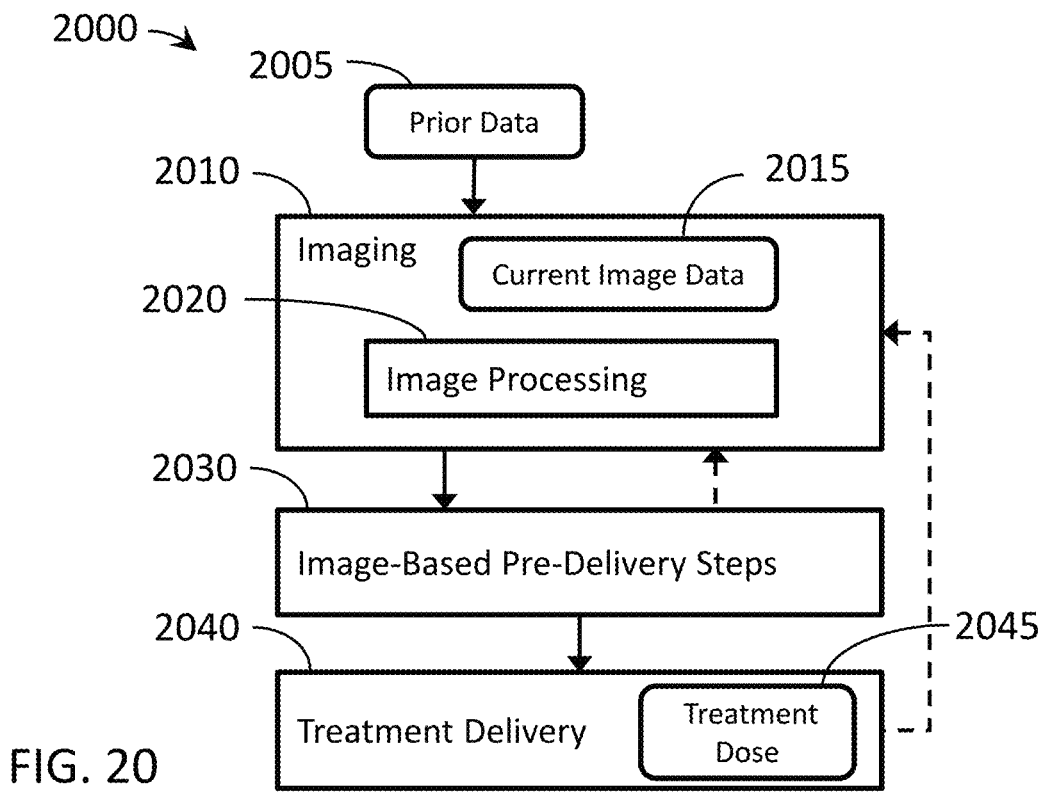
FIG. 20 is a flow chart depicting an exemplary method of IGRT using a radiotherapy device.

FIG. 20 is a flow chart depicting an exemplary method 2000 of IGRT using a radiotherapy device (including, e.g., multimodal apparatus 10). Prior data 2005 can include images of the patient (e.g., a prior image, which may be a previously-acquired planning image, including a prior CT image), treatment plans, phantom information, models, a priori information, etc. In some embodiments, the prior data 2005 is generated by the same radiotherapy device, but at an earlier time. At step 2010, imaging of a patient is performed using a source of radiation (e.g., kV radiation from source 30 and/or MV radiation from source 20 of multimodal apparatus 10). In various embodiments, imaging comprises a helical or circular scan with a fan or cone beam geometry. Step 2010 can produce high-quality (HQ) image(s) or imaging/scan data 2015 using the techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 2010 also includes image processing 2020 to generate patient images based on the imaging/scan data 2015 (e.g., in accordance with methods described above). Although image processing step 2020 is shown as part of imaging step 2010, in some embodiments image processing step 2020 is a separate step, including where image processing is executed by separate devices.

Next, at step 2030, one or more image-based pre-delivery steps, discussed below, are performed based at least in part on the imaging/scan data 2015 from step 2010. As discussed in more detail below, step 2030 can include determining various parameters associated with the therapeutic treatment and (subsequent) imaging planning. In some embodiments, image-based pre-delivery steps (2030) may require more imaging (2010) before treatment delivery (2040). Step 2030 can include adapting a treatment plan based on the imaging data 2015 as part of an adaptive radiotherapy routine. In some embodiments, image-based pre-delivery steps 2030 may include real-time treatment planning. Embodiments may also include simultaneous, overlapping, and/or alternating activation of the imaging and therapeutic radiation sources, as described above. Real-time treatment planning may involve any or all of these types of imaging and therapeutic radiation activation techniques (simultaneous, overlapping, and/or alternating).

Next, at step 2040, therapeutic treatment delivery is performed using a source of high-energy radiation (e.g., MV radiation from radiation source 20). Step 2040 delivers a treatment dose 2045 to the patient according to the treatment plan. In some embodiments, the IGRT method 2000 may include returning to step 2010 for additional imaging at various intervals (e.g., between fractions), followed by image-based pre-delivery steps (2030) and/or treatment delivery (2040) as required. In this manner the high-quality imaging data 2015 may be produced and utilized during IGRT using one apparatus 10 that is capable of adaptive therapy. As mentioned above, steps 2010, 2030, and/or 2040 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 21:
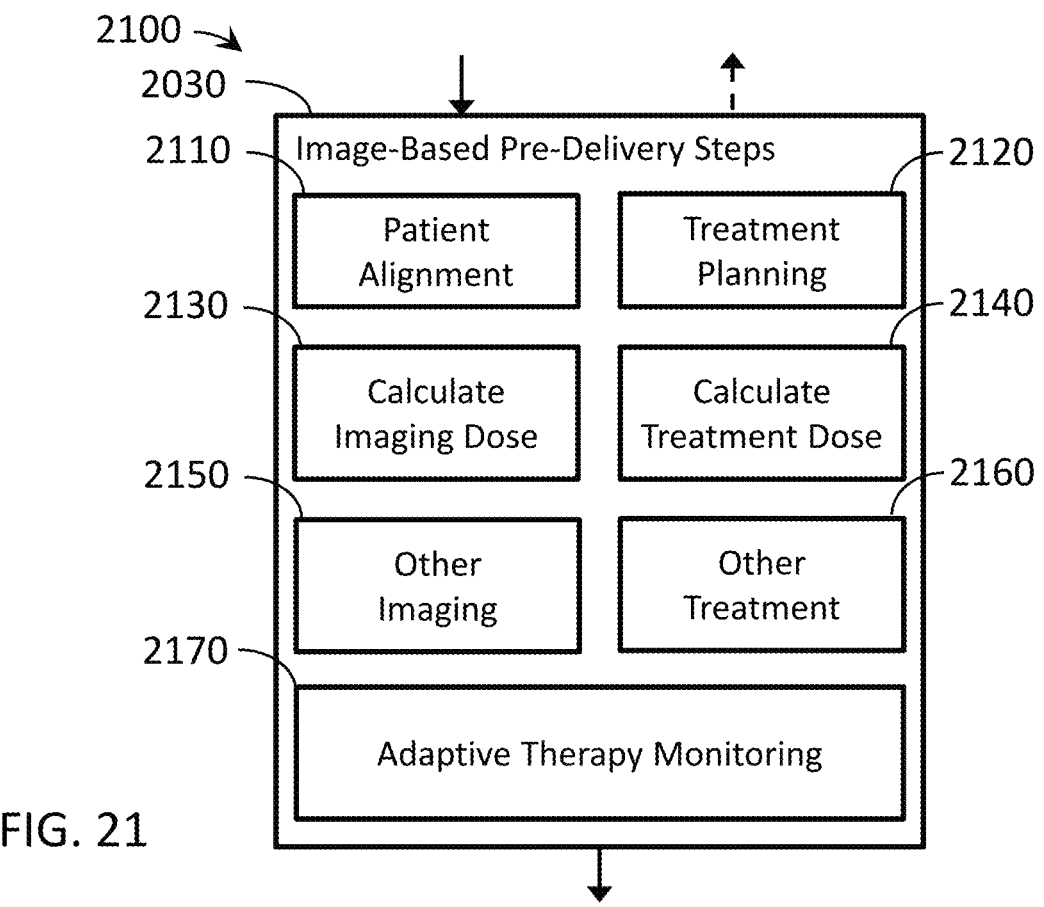
FIG. 21 is a block diagram depicting exemplary image-based pre-delivery steps/options.

FIG. 21 is a block diagram 2100 depicting exemplary image-based pre-delivery steps/options that may be associated with step 2030 above. It will be appreciated that the above-described multimodal apparatus 10 (e.g., as part of a radiotherapy device) can generate low energy (e.g., kV) and high energy (e.g., MV) images that can be used in a variety of ways, including for image-based pre-delivery steps (2030), without departing from the scope of the present invention. For example, images 2015 generated by the radiotherapy device can be used to setup or align a patient prior to treatment (2110). Patient alignment can include correlating or registering the current imaging data 2015 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information. An exemplary patient alignment process is described below.

Images generated by the multimodal apparatus 10 can also be used for treatment planning or re-planning (2120). In various embodiments, step 2120 can include confirming the treatment plan, modifying the treatment plan, generating a new treatment plan, and/or choosing a treatment plan from a set of treatment plans (sometimes referred to as "plan of the day"). For example, if the imaging data 2015 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 2015 (generated by the multimodal apparatus 10 at step 2010), the imaging data 2015 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the multimodal apparatus 10 can be used to calculate imaging dose (2130), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the multimodal apparatus 10 can be used to calculate treatment dose (2140), which may be used for ongoing determinations of total dose to the patient and/or may be included as part of treatment planning or re-planning.

In accordance with other exemplary use cases, images generated by the multimodal apparatus 10 can be used in connection with planning or adjusting other imaging (2150) and/or other treatment (2160) parameters or plans, including, for example, as part of adaptive therapy and/or treatment plan generation. In accordance with another exemplary use case, images generated by the multimodal apparatus 10 can be used in connection with adaptive therapy monitoring (2170), which can include monitoring treatment delivery and adapting as required.

It should be appreciated that the image-based pre-delivery steps (2030) are not mutually exclusive. For example, in various embodiments, calculate treatment dose (2140) can be a step by itself and/or can be part of adaptive therapy monitoring (2170) and/or treatment planning (2120). In various embodiments, the image-based pre-delivery steps (2030) can be performed automatically and/or manually with human involvement.

Figure 22:
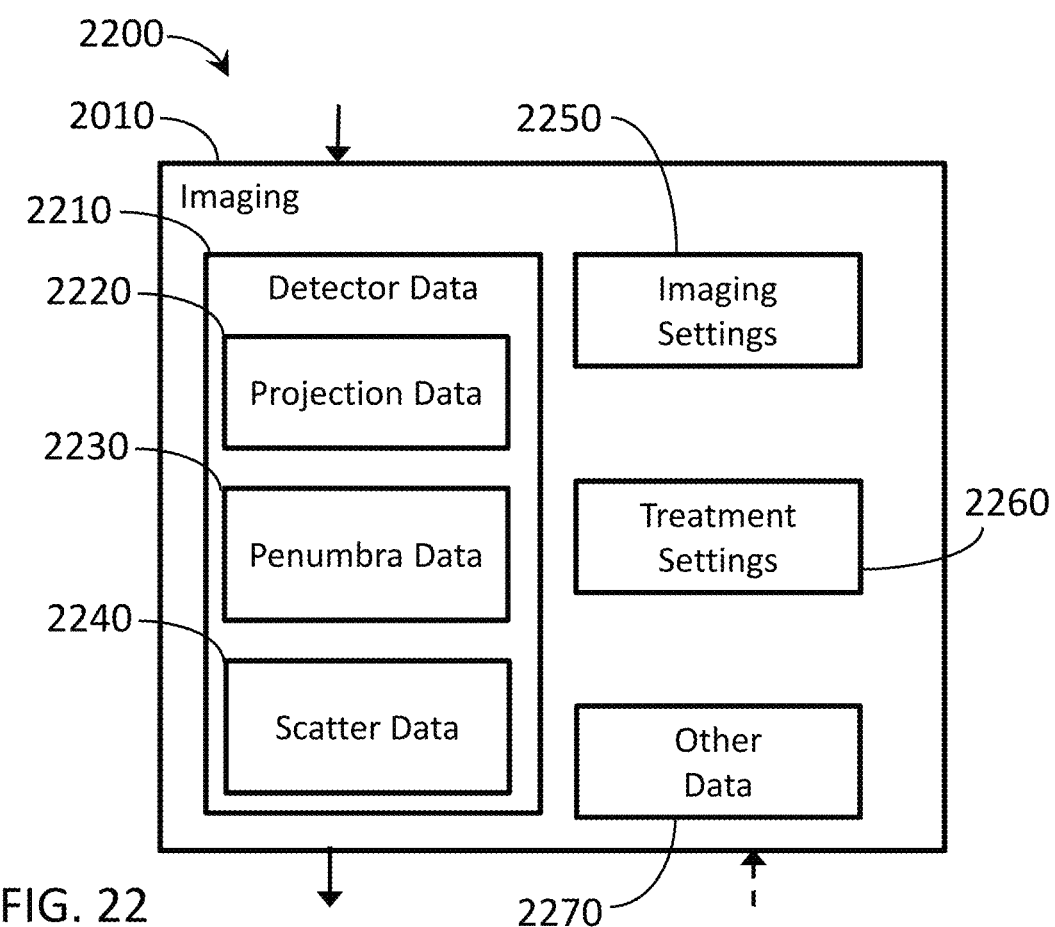
FIG. 22 is a block diagram depicting exemplary data sources that may be utilized during imaging and/or subsequent image-based pre-delivery steps.

FIG. 22 is a block diagram 2200 depicting exemplary data sources that may be utilized during imaging (2010) and/or subsequent image-based pre-delivery steps (2030). Detector data 2210 represents the data received by the radiation detectors (e.g., 24, 34). The projection data 2220 is the data generated by the radiation incident in the collimated beam area, referred to above as the active region. The penumbra data 2230 is the data generated by the radiation incident in the penumbra area. The scatter data 2240 is the data generated by the radiation incident in the peripheral area outside of the penumbra area and/or the determined scatter as described above. In another embodiment, the scatter data 2240 can be used to determine the residual effect of the scatter from the therapeutic radiation source 20 (e.g., MV) when the two sources 20, 30 are operated simultaneously or in an interleaved manner.

In this manner, the penumbra data 2230 and/or the scatter data 2240 may be utilized to improve the quality of the images generated by the imaging step 2010. In some embodiments, the penumbra data 2230 and/or the scatter data 2240 may be combined with the projection data 2220 and/or analyzed in view of the applicable imaging settings 2250, treatment settings 2260 (e.g., if simultaneous imaging and/or treatment radiation), and any other data 2270 associated with the multimodal apparatus 10 at the time of the data collection at the detectors (e.g., 24, 34). In other embodiments, the data may be used for the treatment planning step 2030.

Figure 23:
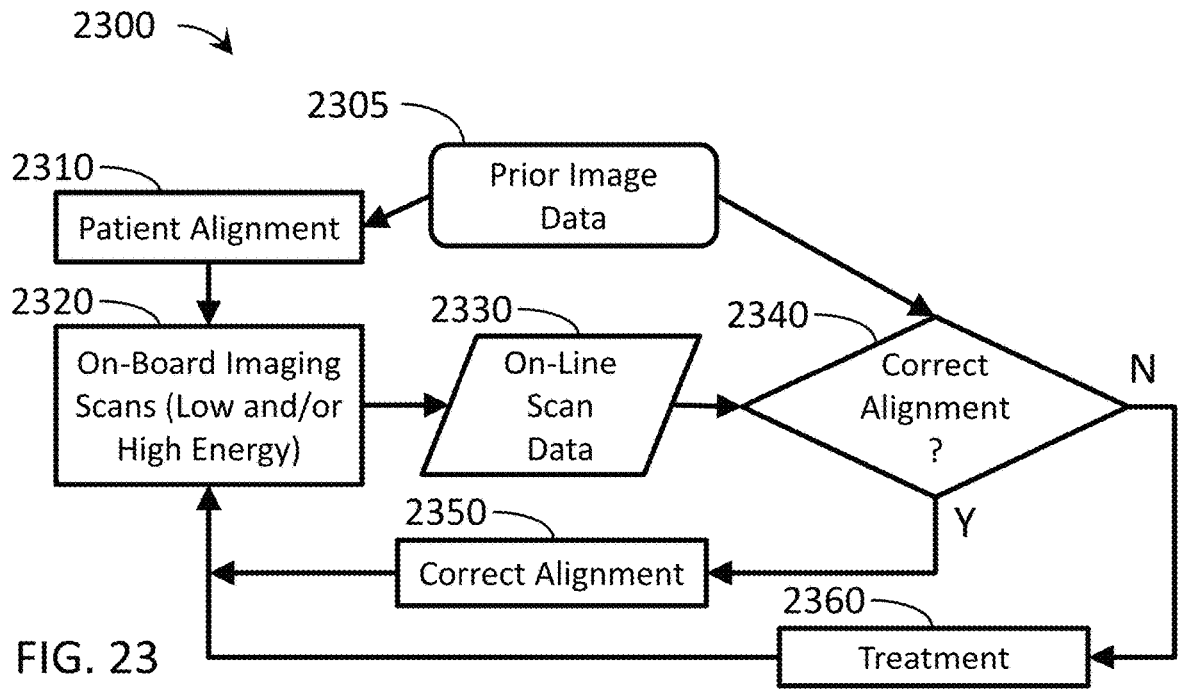
FIG. 23 is a flow chart depicting an exemplary method including patient setup or alignment using a radiotherapy device.
Figure 24:
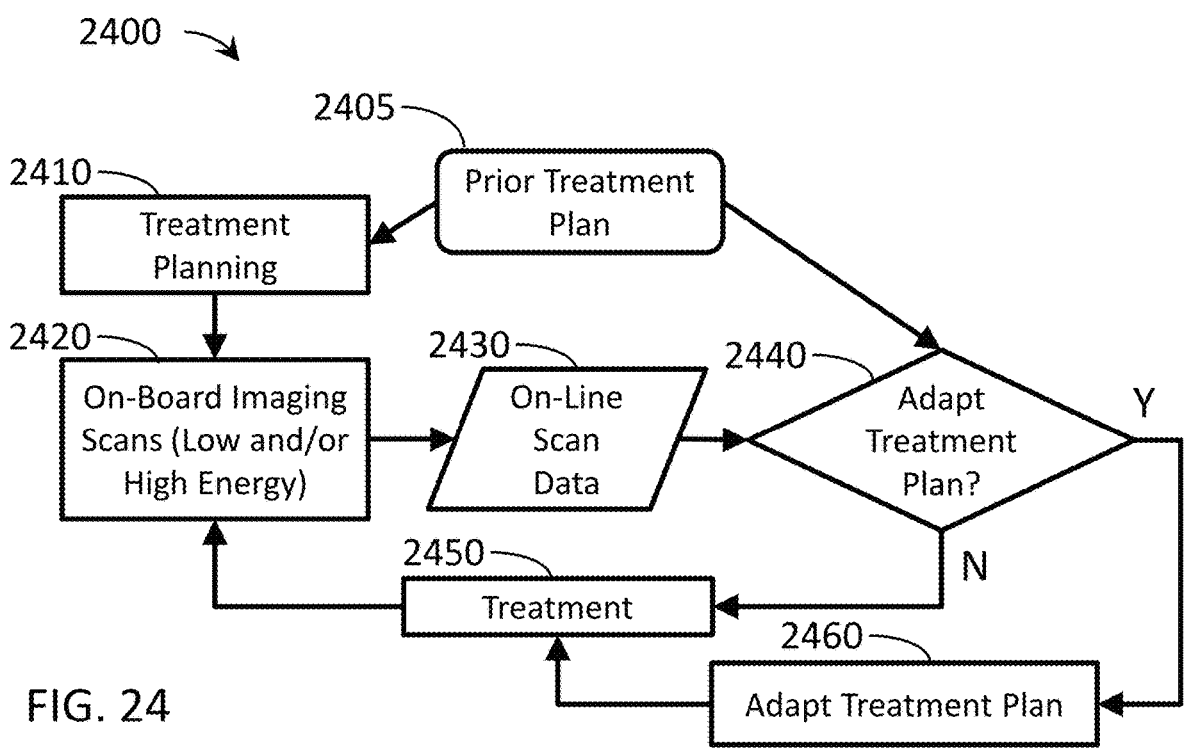
FIG. 24 is a flow chart depicting an exemplary method including adaptive IGRT using a radiotherapy device.

FIGS. 23 and 24 depict exemplary embodiments of imaging 2010, image-based pre-delivery steps 2030, and treatment delivery 2040 use cases, including examples of various forward and feedback sequences associated with on-board imaging using multimodal apparatus 10 during IGRT, including use of the methods described above.

FIG. 23 is a flow chart depicting an exemplary method 2300 including patient setup or alignment using a radiotherapy device (including, e.g., multimodal apparatus 10). Prior data 2305 can include images of the patient (e.g., a prior image, which may be a previously-acquired planning image, including a prior CT image, as discussed above). In some embodiments, the prior data 2305 is generated by the same radiotherapy device, but at an earlier time. At step 2310, an initial or preliminary alignment of the patient can be performed. Then, at step 2320, on-board imaging scans are performed using a low and/or high energy radiation source (e.g., kV radiation from source 30 and/or MV radiation from source 20) of multimodal apparatus 10, including, for example, as described in step 2010 above. In various embodiments, on-board imaging comprises a helical or circular scan with a fan or cone beam geometry. Step 2320 produces on-line imaging/scan data 2330 using the techniques described above. Imaging step 2320 can also include image processing to generate patient images based on the imaging/scan data 2330 (e.g., in accordance with methods described above), including, for example, as described in block 2020 above.

Next, step 2340 determines if an alignment correction is needed based at least in part on the on-line scan data 2330, including, for example, as described in block 2110 above. If an alignment correction or adjustment is needed, the method 2300 proceeds to step 2350 for an alignment correction, based at least in part on the on-line scan data 2330. Then, after the alignment correction, the method can return to step 2320 for additional imaging as a confirmation or further refinement loop. If an alignment correction or adjustment is not needed from step 2340, the method 2300 proceeds to step 2360 for treatment delivery. Then, after treatment, the method 2300 can return to step 2320 for additional imaging as a confirmation or further refinement loop.

FIG. 24 is a flow chart depicting an exemplary method 2400 including adaptive IGRT using a radiotherapy device (including, e.g., multimodal apparatus 10). Prior treatment plans 2405 can include treatment plans as well as images of the patient (e.g., a prior image, which may be a previously-acquired planning image, including a prior CT image, as discussed above), phantom information, models, a priori information, etc. In some embodiments, the prior data 2405 is generated by the same radiotherapy device, but at an earlier time. At step 2410, an initial or preliminary treatment plan can be adopted, for example, based on the prior treatment plan and any additional information. Then, at step 2420, on-board imaging scans are performed using a low and/or high energy radiation source (e.g., kV radiation from source 30 and/or MV radiation from source 20) of multimodal apparatus 10, including, for example, as described in step 2010 above. In various embodiments, on-board imaging comprises a helical or circular scan with a fan or cone beam geometry. Step 2420 produces on-line imaging/scan data 2430 using the techniques described above. Imaging step 2420 can also include image processing to generate patient images based on the imaging/scan data 2430 (e.g., in accordance with methods described above), including, for example, as described in block 2020 above.

Next, step 2440 determines if the treatment plan needs to be re-planned or adapted based at least in part on the on-line scan data 2430, including, for example, as described in block 2120 above. If a treatment plan does not need to be adapted or re-planned, the method 2400 proceeds to step 2450 for treatment delivery. If a treatment plan does need to be adapted or re-planned, the method 2400 proceeds to step 2460 for adapting the treatment plan, based at least in part on the on-line scan data 2430. Then, after adapting the treatment plan, the method can proceed to step 2450 for treatment delivery. Then, after treatment, the method 2400 can return to step 2420 for additional imaging as a confirmation or further refinement loop.

In some embodiments, methods 2300, 2400 and other methods can be executed simultaneously or in an interleaved manner based on a preferred workflow. For example, an on-board imaging scan can be performed and utilized as both the 2320 and 2420 scans to confirm treatment and continued alignment at the same time using the same data. In other embodiments, two or more of the image-based pre-delivery steps 2030 can be executed simultaneously or in an interleaved manner based on a preferred workflow, including where the same imaging data 2015 and/or image processing 2020 is utilized for more than one of the image-based pre-delivery steps 2030.

Various other embodiments can include other use cases with on-board imaging using multimodal apparatus 10 during IGRT. For example, image "merge" with the planning CT (pCT) for delivery analysis and/or re-planning with an MVCT. In this dose calculation embodiment, the kV scan can be a narrow, very-low-dose "pilot" beam for finding the skin-air interface at each angle, such that the pCT can be properly deformed to the body outline at the time of each fraction.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A multimodal imaging apparatus, comprising:
a rotatable gantry system positioned at least partially around a patient support;
a first radiation source coupled to the rotatable gantry system, the first radiation source configured for imaging radiation;
a first beamformer configured to adjust a shape of a first radiation beam emitted by the first radiation source;
a second radiation source coupled to the rotatable gantry system, the second radiation source configured for at least one of imaging radiation or therapeutic radiation, wherein the second radiation source comprises an energy level more than the first radiation source;
a second beamformer configured to adjust a shape of a second radiation beam emitted by the second radiation source; and
at least one radiation detector coupled to the rotatable gantry system and positioned to receive radiation from at least one of the first radiation source and the second radiation source;
wherein the apparatus acquires first measured projection data associated with a first region of a patient from the first radiation source and second measured projection data associated with a second region of the patient from the second radiation source during a scan and at least one of:
augments the first measured projection data using the second measured projection data; and
augments the second measured projection data using the first measured projection data.

2. The apparatus of claim 1, wherein the first source of radiation comprises a kilo-electron volt peak photon energy (keV) up to 150 keV and the second source of radiation comprises a mega-electron volt peak photon energy (MeV) of 1 MeV or greater.

3. The apparatus of claim 1, wherein the second radiation source comprises a peak energy of 3 MeV and an average energy of about 1 MeV.

4. The apparatus of claim 1, further comprising a data processing system configured to:
receive the first measured projection data and the second measured projection data; and
combine the first measured projection data and the second measured projection data for processing data or reconstructing an image of the patient.

5. The apparatus of claim 1, wherein the first measured projection data and the second measured projection data are acquired simultaneously or less than or equal to 50 ms from each other.

6. The apparatus of claim 1, wherein the first region and the second region overlap each other.

7. The apparatus of claim 1, wherein the first measured projection data is truncated in the second region or the second measured projection data is truncated in the first region.

8. The apparatus of claim 1, wherein the scan comprises a helical scan.

9. The apparatus of claim 1, wherein:
the at least one radiation detector comprises:
a first detector coupled to the rotatable gantry system and positioned to receive radiation from the first radiation source; and
a second detector coupled to the rotatable gantry system and positioned to receive radiation from the second radiation source;
the second beamformer and the second detector are configured such that the second radiation beam projects through the second region in a transaxial plane of the patient and does not project through all of the first region in the transaxial plane of the patient;
the first beamformer and the first detector are configured such that the first radiation beam projects through the first region of the patient; and
estimated projection data from the second radiation source in the first region is based on the first measured projection data.

10. The apparatus of claim 9, wherein the first region comprises a peripheral region of the patient and the second region comprises a central region of the patient.

11. The apparatus of claim 9, wherein the first radiation beam and the second radiation beam overlap in the transaxial plane.

12. The apparatus of claim 9, wherein a maximum transaxial field-of-view available via the second detector is less than a width of the patient in the transaxial plane.

13. The apparatus of 1, wherein the first beamformer comprises:
a first aperture configured such that the first radiation beam projects through a target region in a transaxial plane of the patient via the first aperture; and
a second aperture configured such that the first radiation beam projects through a peripheral region in the transaxial plane of the patient via the second aperture;
wherein the target region and the peripheral region do not overlap in the transaxial plane; and
the at least one radiation detector comprises a first detector coupled to the rotatable gantry system and positioned to receive radiation from the first radiation source, wherein the first detector is in a fixed position with an outermost edge of the first detector located outside of an outermost projected patient boundary during the scan.

14. The apparatus of 13, wherein estimated projection data from the first radiation source between the target region and the peripheral region is based on the second measured projection data.

15. The apparatus of 14, wherein:
the at least one radiation detector comprises a second detector coupled to the rotatable gantry system and positioned to receive radiation from the second radiation source; and
the second beamformer and the second detector are configured such that the second radiation beam projects through an intermediate region between the target region and the peripheral region in the transaxial plane of the patient;
wherein the intermediate region overlaps the target region and the peripheral region in the transaxial plane.

16. The apparatus of 1, wherein:
the at least one radiation detector comprises a first detector coupled to the rotatable gantry system and positioned to receive radiation from the first radiation source, wherein the first beamformer and the first detector are configured in a transaxial plane such that the first radiation beam projects through every point of a target region of the patient during the scan;

wherein for any angular location of the first radiation source, any transaxial point in the target region of the patient is visible by the first radiation source at any sampled azimuth angle, and wherein the first beamformer is dynamically collimated during the scan.

17. The apparatus of 16, wherein:

the first beamformer and the first detector are configured in an axial direction such that a first axial field-of-view (FOV) associated with the first radiation source is larger than a second axial FOV associated with the second radiation source;

the first beamformer and the first detector are configured in a transaxial direction such that for any angular location of the first radiation source, any point in a first transaxial FOV associated with the first radiation source and in the second axial FOV associated with the second radiation source is visible by the first radiation source at any sampled azimuth angle;

estimated projection data from the second radiation source is based on the first measured projection data when projections of the patient extend beyond the second transaxial FOV; and the image is used for material decomposition within an overlapped region of the first transaxial FOV and the second transaxial FOV, resulting in basis material images.

18. The apparatus of claim 1, wherein the first radiation source is coupled to a first rotatable gantry of the rotatable gantry system and the second radiation source is coupled to a second rotatable gantry of the rotatable gantry system.

19. A method of acquiring projection data from a multi-modal imaging apparatus, comprising:

receiving first measured projection data associated with a first region of a patient from a first radiation source, the first radiation source configured for imaging radiation;

receiving second measured projection data associated with a second region of the patient from a second radiation source, the second radiation source configured for at least one of imaging radiation or therapeutic radiation, wherein the second radiation source comprises an energy level more than the first radiation source;

providing the first measured projection data and the second measured projection data for reconstructing an image of the patient, the reconstructing comprising at least one of:

augmenting the first measured projection data using the second measured projection data; and augmenting the second measured projection data using the first measured projection data.

20. The method of claim 19, wherein the first measured projection data and the second measured projection data are acquired simultaneously or within about 50 ms of each other.

21. A radiotherapy delivery device comprising:

a rotatable gantry system positioned at least partially around a patient support;

a first radiation source coupled to the rotatable gantry system, the first radiation source configured for imaging radiation;

a first beamformer configured to adjust a shape of a first radiation beam emitted by the first radiation source;

a second radiation source coupled to the rotatable gantry system, the second radiation source configured for at least one of imaging radiation or therapeutic radiation, wherein the second radiation source comprises an energy level more than the first radiation source;

a second beamformer configured to adjust a shape of a second radiation beam emitted by the second radiation source; and at least one radiation detector coupled to the rotatable gantry system and positioned to receive radiation from at least one of the first radiation source or the second radiation source; and a data processing system configured to:

receive first measured projection data from the first radiation source and second measured projection data from the second radiation source;

at least one of:

augment the first measured projection data using the second measured projection data; and augment the second measured projection data using the first measured projection data; and combine the first measured projection data and the second measured projection data to reconstruct an image for online adaptive IGRT.

* * * * *